(12) United States Patent
Matsushita

(10) Patent No.: US 10,548,822 B2
(45) Date of Patent: Feb. 4, 2020

(54) BEAUTY CARE METHOD

(71) Applicant: MTG Co., Ltd., Nagoya-shi (JP)

(72) Inventor: Tsuyoshi Matsushita, Nagoya (JP)

(73) Assignee: MTG Co., Ltd., Nagoya-shi (JP)

( * ) Notice: Subject to any disclaimer, the term of this patent is extended or adjusted under 35 U.S.C. 154(b) by 607 days.

(21) Appl. No.: 15/106,933

(22) PCT Filed: Nov. 4, 2014

(86) PCT No.: PCT/JP2014/079275
§ 371 (c)(1),
(2) Date: Jun. 21, 2016

(87) PCT Pub. No.: WO2015/098295
PCT Pub. Date: Jul. 2, 2015

(65) Prior Publication Data
US 2018/0193238 A1    Jul. 12, 2018

(30) Foreign Application Priority Data

Dec. 25, 2013 (JP) ................................ 2013-266211
Feb. 11, 2014 (JP) ................................ 2014-023921

(51) Int. Cl.
*A61K 8/19* (2006.01)
*A61Q 19/00* (2006.01)
(Continued)

(52) U.S. Cl.
CPC .............. *A61K 8/19* (2013.01); *A61K 8/0212* (2013.01); *A61K 8/0241* (2013.01); *A61K 8/345* (2013.01);
(Continued)

(58) Field of Classification Search
CPC .... A61K 8/19; A61K 8/0212; A61K 2800/47; A61K 8/0241; A61K 8/676;
(Continued)

(56) References Cited

U.S. PATENT DOCUMENTS

| 4,046,591 A | 9/1977 | Laguerre |
| 2003/0073022 A1* | 4/2003 | Hultman ................ G03G 9/107 |
| | | 430/111.31 |

(Continued)

FOREIGN PATENT DOCUMENTS

| CN | 101357105 A | 2/2009 |
| EP | 1 694 284 A1 | 8/2006 |

(Continued)

OTHER PUBLICATIONS

Notification of Reasons for Refusal dated Nov. 14, 2017 in Japanese Patent Application No. 2014-023921 (with English translation Downloaded from Global Dossier in the EPO website).

(Continued)

*Primary Examiner* — Kevin C Sirmons
*Assistant Examiner* — Leah J Swanson
(74) *Attorney, Agent, or Firm* — Oblon, McClelland, Maier & Neustadt, L.L.P.

(57) ABSTRACT

A beauty care method has a step of applying an aqueous pack agent 1 containing water, a magnetic powder 11, a thickener and a charged iontophoretic component 13 to the skin 2; a step of applying magnetic force to the magnetic powder 11 in the aqueous pack agent 1 applied to the skin 2 to attract and remove the magnetic powder 11 from the skin surface 21 by the magnetic force while leaving an aqueous solution 12 of the iontophoretic component on the skin surface 21; and a step of applying an iontophoretic current to the skin 2 with the aqueous solution 12 left to allow the iontophoretic component 13 to infiltrate into the skin.

11 Claims, 11 Drawing Sheets

(51) Int. Cl.
*A61N 1/30* (2006.01)
*A61N 1/32* (2006.01)
*A61K 8/67* (2006.01)
*A61K 8/02* (2006.01)
*A61K 8/34* (2006.01)

(52) U.S. Cl.
CPC ............... *A61K 8/676* (2013.01); *A61N 1/30* (2013.01); *A61N 1/325* (2013.01); *A61Q 19/00* (2013.01); *A61K 2800/412* (2013.01); *A61K 2800/47* (2013.01); *A61K 2800/48* (2013.01); *A61K 2800/83* (2013.01)

(58) Field of Classification Search
CPC ...... A61K 2800/83; A61N 1/30; A61N 1/325; A61N 1/327; A61Q 19/00; A61Q 19/02; A45D 2200/1063
USPC .......................................................... 604/501
See application file for complete search history.

(56) References Cited

U.S. PATENT DOCUMENTS

| | | | |
|---|---|---|---|
| 2007/0009560 A1 | 1/2007 | Golz-Berner et al. | |
| 2007/0148105 A1 | 6/2007 | Spector | |
| 2007/0148112 A1* | 6/2007 | Dingley | A61K 8/0212 424/63 |
| 2007/0292463 A1 | 12/2007 | Spector | |
| 2009/0110704 A1 | 4/2009 | Redaelli | |
| 2012/0271219 A1* | 10/2012 | Weisgerber | A61B 18/1206 604/20 |
| 2013/0006040 A1 | 1/2013 | Lee | |
| 2013/0315846 A1* | 11/2013 | Collier | A61K 8/97 424/59 |

FOREIGN PATENT DOCUMENTS

| | | | |
|---|---|---|---|
| EP | 3 075 374 A1 | 10/2016 | |
| JP | 61-3765 B2 | 2/1986 | |
| JP | 64-68313 A | 3/1989 | |
| JP | 2003-199620 A | 7/2003 | |
| JP | 2004-155720 A | 6/2004 | |
| JP | 2004-224782 A | 8/2004 | |
| JP | 2005-239563 A | 9/2005 | |
| JP | 2005-312497 A | 11/2005 | |
| JP | 2007-131547 A | 5/2007 | |
| JP | 4768404 B2 | 9/2011 | |
| JP | 2013-1685 A | 1/2013 | |
| JP | 2013-521925 A | 6/2013 | |
| RU | 2 147 430 C1 | 4/2000 | |
| RU | 2 484 809 C2 | 6/2013 | |
| WO | WO 2005/041915 A1 | 5/2005 | |
| WO | WO 2006/131997 A1 | 12/2006 | |
| WO | WO-2007104089 A1 * | 9/2007 | ............ A61K 8/02 |
| WO | WO 2015/079942 A1 | 6/2015 | |

OTHER PUBLICATIONS

Extended European Search Report dated Nov. 29, 2017 in corresponding European Patent Application No. 14875841.0, 9 pages.
International Search Report dated Feb. 17, 2015 in PCT/JP2014/079275, filed Nov. 4, 2014.
Office Action dated Jun. 7, 2018 in Japanese Patent Application No. 2014-023921 (with unedited computer generated English translation), 6 pages.
Combined Taiwanese Office Action and Search Report dated Apr. 18, 2018 in Taiwanese Patent Application No. 103138909 (with English translation), 15 pages.
Combined Chinese Office Action and Search Report dated Apr. 17, 2018 in Patent Application No. 201480071088.4 (with English language translation and English translation of categories of cited documents), 17 pages.
Combined Russian Office Action and Search Report dated May 31, 2018 in Patent Application No. 2016130042/14(046756) (with English language translation), 13 pages.
Examination report dated Dec. 10, 2018 in corresponding Australian Patent Application No. 2014371743, 4 pages.
European Office Action dated Oct. 23, 2018 in Patent Application No. 14 875 841.0, 5 pages.
Communication pursuant to Article 94(3) EPC dated Apr. 23, 2019 in European Patent Application No. 14 875 841.0, 3 pages.
Combined Chinese Office Action and Search Report dated Mar. 5, 2019 in Chinese Patent Application No. 201480071088.4 (with English translation and English translation of Category of Cited Documents), 13 pages.
Taiwanese Office Action dated Mar. 15, 2019 in Taiwanese Patent Application No. 103138909 (with English translation), 7 pages.
European Office Action in patent application No. 148758410.0 dated Oct. 4, 2019.

* cited by examiner

BEAUTY CARE METHOD

TECHNICAL FIELD

The present invention relates to a beauty care method for skin beauty.

BACKGROUND ART

As a beauty care method for skin beauty, a method in which a pack agent is used is known. The pack agent is constituted to remove e.g., dirt and waste of the skin together with a used pack agent. Methods for removing such a used pack agent from the skin conventionally range from wiping with e.g., cotton to washing away with e.g., warm water. Recently, easier methods than these conventional ones have been desired for removing a used pack agent.

For example, Patent Document 1 proposes a skin cleaning cream, which is prepared by adding a powder constituted of magnetized particles or particles that can be magnetized to an excipient serving as an application base. The skin cleaning cream is, for example, used as follows: after the skin cleaning cream is applied to the skin, a magnet or the like is allowed to approach the skin cleaning cream on the skin surface. Therefore, a magnetic force acts on the powder contained in the skin cleaning cream, and attracts the powder. Subsequently, the used skin cleaning cream attached to the powder and dirt of the skin and others are attracted and removed by the magnetic force from the skin surface together with the powder. In this manner, the skin cleaning cream is easily removed from the skin surface.

In the meantime, after removing dirt of the skin and others by use of the pack agent, it is also effective for skin beauty to allow beauty components such as nutritional components that supply nutritive substance to the skin and a whitening ingredient for producing a whitening effect to infiltrate into the skin to obtain beauty effects of these beauty components. For example, Patent Document 2 discloses a method for promoting infiltration of a beauty component by iontophoresis. The iontophoresis is a method of promoting infiltration of a beauty component to the skin by applying a weak current to a desired part into which the beauty component is to be supplied to allow a charged beauty component to migrate into the skin.

PRIOR ART DOCUMENT

Patent Document

Patent Document 1: JP-B-61-3765
Patent Document 2: JP-B-4768404

SUMMARY OF THE INVENTION

Problem to be Solved by the Invention

A higher beauty effect can be obtained by carrying out removal of dirt of the skin and others by the pack agent and iontophoresis in succession. However, for carrying out these in succession, there are the following problems.

More specifically, a conventional pack agent containing a magnetic powder uses an excipient containing an oily ingredient such as Vaseline as a main component. Because of this, the oily ingredient at least partly remains on the skin surface and forms an oil film after the pack agent is attracted and removed from the skin by the magnetic force. In addition, since the oil film is insulative, it is difficult to apply a weak current to the skin for iontophoresis.

As mentioned above, it is difficult for a conventional pack agent containing a magnetic powder to carry out attraction and removal of dirt of the skin and others and iontophoresis in succession, and the oil film must be removed from the skin surface before iontophoresis. For the reason, an excellent beauty effect produced by carrying out removal of dirt of the skin and others and iontophoresis in succession is rarely obtained. Since a step of removing the oil film from the skin surface must be performed in addition to removal of a used pack agent and iontophoresis, the working process becomes complicated.

To avoid the aforementioned problem, a method in which an aqueous pack agent that rarely forms the oil film on the skin surface is used is conceivable. However, in the case, it is difficult to obtain a pack agent in a paste-like appearance suitable for application to the skin by adding a magnetic powder to an aqueous pack agent.

The present invention has been made in view of the aforementioned background and is directed to providing a beauty care method that can provide a more excellent beauty effect by a simple procedure.

Means for Solving the Problem

According to an aspect of the present invention, there is provided a beauty care method having
a step of applying an aqueous pack agent containing a water, a magnetic powder, a thickener and a charged iontophoretic component to the skin,
a step of applying magnetic force to the magnetic powder in the aqueous pack agent applied to the skin to attract and remove the magnetic powder from the skin surface while leaving an aqueous solution of the iontophoretic component on the skin surface, and
a step of applying an iontophoretic current to the skin with the aqueous solution left to allow the iontophoretic component to infiltrate into the skin.

Effects of the Invention

In the beauty care method, first, the step of applying an aqueous pack agent to the skin is carried out. Since the aqueous pack agent contains a water, a magnetic powder and a thickener, the magnetic powder is dispersed in the aqueous pack agent and the aqueous pack agent is obtained in a paste-like appearance suitable for application to the skin, with the result that the user feels smooth application to the skin.

Then, the step of applying a magnetic force to the magnetic powder in the aqueous pack agent applied to the skin to attract and remove the magnetic powder from the skin surface is carried out. In this step, the magnetic powder is attracted and removed from the skin surface by the magnetic force; at the same time, the used aqueous pack agent attached to the magnetic powder and dirt of the skin and others are attracted and removed from the skin surface by the magnetic force.

Since the aqueous pack agent is aqueous, an oil film is rarely formed on the skin surface after the used aqueous pack agent is attracted and removed. Thus, the amount of a substance which inhibits the infiltration of a beauty component, such as dirt of a skin, waste or an oil film, is low on the skin surface after the aqueous pack agent is attracted and removed. The resultant skin surface is in the state where a beauty component easily infiltrates. Since an iontophoretic component is blended in advance in the aqueous pack agent, the aqueous solution containing the ionized iontophoretic component can remain applied onto the skin surface even though the aqueous pack agent is attracted and removed from the skin surface.

Thereafter, a step of applying an iontophoretic current to the skin on which the aqueous solution is applied, to allow the iontophoretic component to infiltrate into the skin, is carried out. As described above, the aqueous pack agent rarely forms an oil film on the skin surface after the attraction and removal. Accordingly, after the aqueous pack agent is attracted and removed from the skin surface, an iontophoretic current can be applied to the skin without removing the oil film. Owing to this, the charged iontophoretic component can be allowed to migrate into the skin, and infiltration of the iontophoretic component into the skin can be facilitated. As mentioned above, iontophoresis cannot be carried out immediately after a pack agent is attracted and removed by in conventional pack agents containing an oily ingredient as a main component.

As mentioned above, in the beauty care method, an aqueous pack agent is applied to the skin and then the aqueous pack agent is attracted and removed by the magnetic force. Owing to the sequential operations, a working step of attracting and removing dirt of the skin and others and a working step of applying an aqueous solution containing an iontophoretic component to the skin can be continuously carried out, and further iontophoresis can be continuously carried out. Accordingly, an excellent beauty effect can be easily obtained by carrying out removal of dirt of the skin and others and iontophoresis in succession. Since a working step of removing an oil film from the skin surface is not required between the removal of skin dirt and the iontophoresis, the working process can be further simplified.

As described in the foregoing, according to the beauty care method, a beauty effect can be more excellently obtained by simple steps.

MODE FOR CARRYING OUT THE INVENTION

Figure 1:
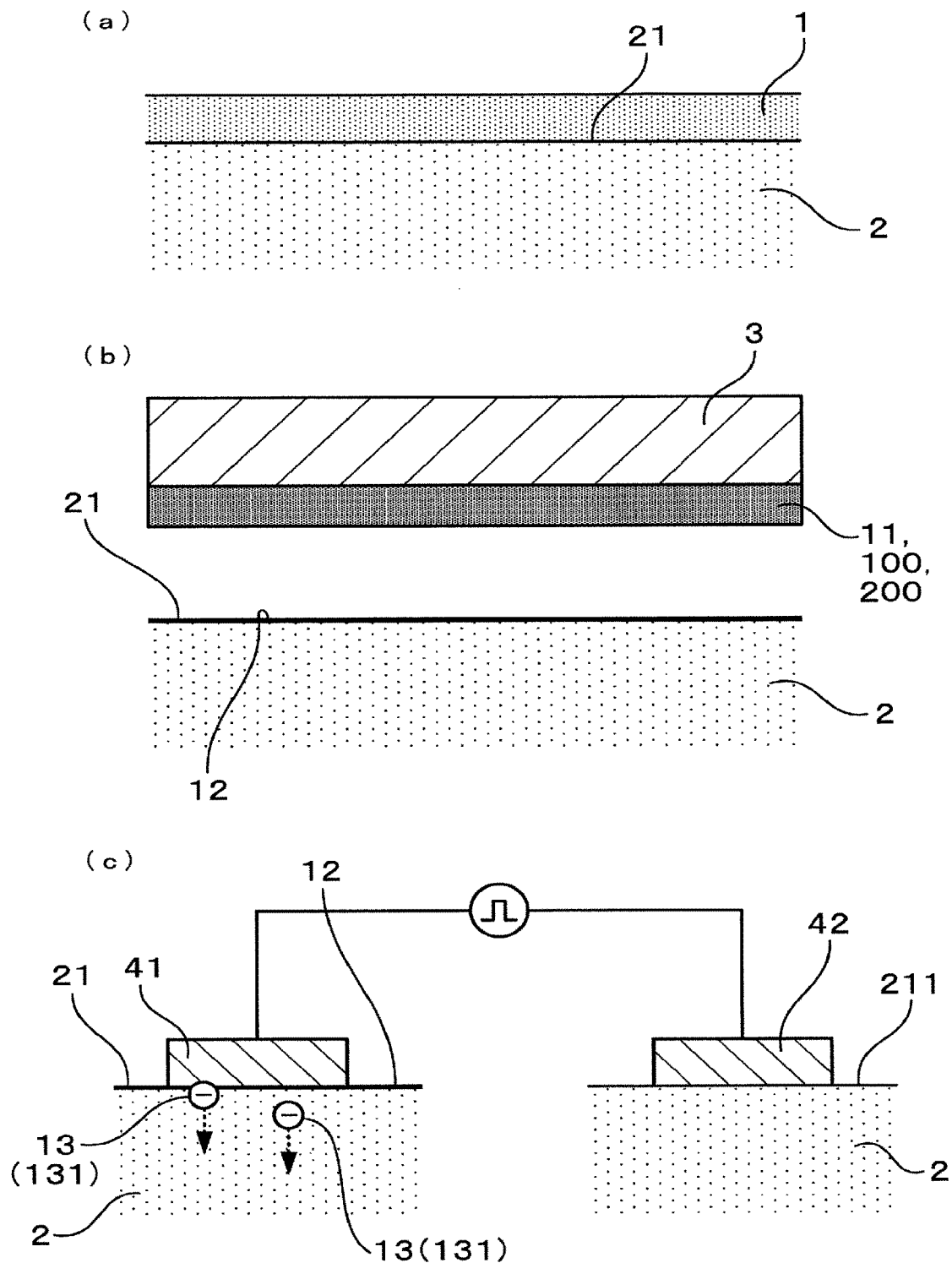
FIG. 1(a) is an illustration of a state in which an aqueous pack agent is applied in Example 1, (b) is an illustration of a state in which the aqueous pack agent is attracted and removed by the magnetic force, and (c) is an illustration of a state in which iontophoresis is carried out.

In the beauty care method, the iontophoresis is carried out by bringing two electrodes into contact with the skin and applying an iontophoretic current between the two electrodes. In the following description, one of the two electrodes is called as a working electrode and the other electrode is called as a counter electrode, for convenience sake. The working electrode is defined as the electrode to be brought into contact with a desired part in which an iontophoretic component is allowed to infiltrate.

The iontophoretic current is a current having a single-polarity and exhibiting various waveforms, such as DC current, pulse current and so on. The polarity of the iontophoretic current is defined in conformity to the polarity of the charge of the iontophoretic component. For example, if the iontophoretic component is present in the state of a negative ion in the aqueous solution, a voltage is applied between the two electrodes such that the electrical potential of the working electrode is lower than that of the counter electrode. In this manner, an iontophoretic current flows between the working electrode serving as a cathode and the counter electrode serving as an anode. the iontophoretic component is repelled from the working electrode and migrates to the counter electrode sides, i.e., into the skin. As a result, infiltration of the iontophoretic component into the skin is facilitated.

The current value of the iontophoretic current can be specified to fall within the range of, for example, 100 to 1000 µA. If the current value of the iontophoretic current is less than 100 µA, the effect of facilitating infiltration of a beauty component into the skin may be insufficient and the beauty effect that the user can feel may decrease. If the current value of the iontophoretic current exceeds 1000 µA, the effect of facilitating infiltration of a beauty component almost reaches a plateau.

As the current value of the iontophoretic current increases, infiltration of a beauty component into the skin is facilitated; whereas, in some cases, the user may feel a sense of discomfort at a contact part of the skin with the working electrode. To sufficiently obtain the effect of facilitating infiltration of the beauty component while avoiding such a problem, the current value of the iontophoretic current is preferably set to be 100 to 240 µA.

For the aqueous pack agent, the solvent can be appropriately selected to obtain desired properties such as texture and spreadability when applied to the skin and to obtain a paste-like appearance sufficient to be applied to the skin. For example, the aqueous pack agent may contain a water as a solvent. In this case, since the aqueous pack agent contains the charged iontophoretic component, an aqueous solution containing the iontophoretic component remains on the skin surface after the magnetic powder is removed from the skin, as described above.

The solvent of the aqueous pack agent may be constituted of a water-soluble solvent alone without water. As the water-soluble solvent, for example, a water soluble alcohol such as ethanol and isopropyl alcohol, and glycerin can be used. In this case, the aqueous pack agent must contain a component, such as ascorbate, which is constituted to produce an iontophoretic component when dissolved in water. In the case of the aqueous pack agent designed in this way, when a magnetic powder is removed from the skin, the aforementioned component remains on the skin surface. The component remaining on the skin surface is ionized with moisture that the skin itself has or moisture in the air and produces an iontophoretic component. Because of this, even if the aqueous pack agent does not contain water, iontophoresis can be performed.

In the aqueous pack agent to be used in the beauty care method, the more the content of a component insoluble in water decreases, the more rarely the aqueous pack agent forms an oil film on the skin surface and the easier the aqueous pack agent has excellent performance. Accordingly, in the aqueous pack agent, if the total of components excluding a magnetic powder is specified as 100 mass %, the content of a component insoluble in water is limited to be 50 mass % or less. In order to suppress formation of an oil film on the skin surface, the content of the component insoluble in water is preferably 40 mass % or less and more preferably 30 mass % or less.

If a water is contained in the aqueous pack agent as a solvent, a thickener must be contained together with water. The thickener has an action of increasing the viscosity of the aqueous pack agent such that the aqueous pack agent has an appropriate viscosity. Accordingly, the magnetic powder is easily dispersed in the aqueous pack agent, and a paste-like aqueous pack agent suitable for application to the skin is easily obtained. The thickener also has an action of adhering particles constituting the magnetic powder when applied to the skin. Thus, in the aqueous pack agent, particles of the magnetic powder easily adhere to each other, with the result that the used aqueous pack agent is easily removed from the skin surface in the form of a continuous film. Consequently, the aqueous pack agent can be easily attracted and removed from the skin surface, and the used aqueous pack agent and fine particles in the magnetic powder are suppressed from remaining on the skin surface.

In the case where an aqueous pack agent does not contain a thickener, since the viscosity of the aqueous pack agent does not increase, some problems occur such as precipitation of the magnetic powder by gravity, dripping of the aqueous pack agent from the skin surface due to low viscosity and so on. Because of these problems, it is difficult to apply such an aqueous pack agent to the skin.

As the thickener, a conventional thickener for use in cosmetics can be used. Examples of the thickener include a glycerin, (acrylates/alkyl acrylate (C10-30)) cross polymer, a cellulose derivative, xanthan gum, guar gum, starch and a derivative thereof, alginate and a derivative thereof, agar, sodium polyacrylate, a carboxyvinyl polymer and bentonite. These thickeners may be used alone or in combination.

The aqueous pack agent preferably contains 10 to 45 mass % of glycerin relative to the total aqueous pack agent, as a thickener. In this case, the adhesive force acting between particles of the magnetic powder increases, a continuous film-like structure of the aqueous pack agent tends not to easily tear when the used aqueous pack agent is attracted and removed from the skin. As a result, the aqueous pack agent is more easily attracted and removed from the skin surface and the used aqueous pack agent and others can be prevented from remaining on the skin surface.

The content of water serving as a solvent is preferably 5 to 73 mass % relative to the total aqueous pack agent. If the content of water falls within a specific range as mentioned above, the aqueous pack agent tends to be obtained in a smooth paste-like appearance, in which the magnetic powder is dispersed. As a result, the aqueous pack agent is easily spread over when applied to the skin and the user feels smooth spreading over the skin.

If the content of water is less than 5 mass %, the aqueous pack agent is lack of moisture and may be formed into a sticky mass. In this case, the user may feel un-comfortability such as roughness when the aqueous pack agent is brought into contact to the skin. In some cases, the aqueous pack agent brought into contact to the skin may cause an extremely strong stimulus to the skin.

Consequently, it becomes difficult to spread the aqueous pack agent over the skin. To obtain an aqueous pack agent having a paste-like appearance suitable for application to the skin, the content of water is preferably 5 mass % or more and more preferably 6 mass % or more.

In contrast, if the content of water exceeds 73 mass %, it is difficult to obtain an effect of increasing viscosity due to a thickener, with the result that the viscosity of the aqueous pack agent may be extremely reduced. In this case, the amount of magnetic powder contained in the aqueous pack agent applied to the skin surface becomes insufficient due to precipitation of the magnetic powder by gravity. If the amount of magnetic powder is insufficient, the magnetic force acting on the whole magnetic powder becomes insufficient when a magnet or the like is allowed to approach. In some cases, the used aqueous pack agent and others conceivably remain on the skin surface. Also in this case, due to low viscosity, the aqueous pack agent may drip from the skin surface. Thus, in order to obtain an aqueous pack agent having an appropriately large viscosity, the content of water is preferably 73 mass % or less, more preferably 30 mass % or less and further preferably 15 mass % or less.

It is preferable that the content of the magnetic powder relative to the whole aqueous pack agent is 15 to 80 mass %. In this case, since the amount of magnetic powder contained in the aqueous pack agent applied to the skin is relatively large, the magnetic force acting on the whole magnetic powder increases when a magnet or the like is allowed to approach the aqueous pack agent. As a result, the used aqueous pack agent can be easily attracted and removed from the skin surface together with dirt of the skin and others, and the aqueous pack agent and others can be prevented from remaining on the skin surface.

If the content of the magnetic powder is less than 15 mass %, since the content of the magnetic powder is low, when a magnet or the like is allowed to approach, the magnetic force acting on the whole magnetic powder may become insufficient. As a result, it becomes difficult to attract and remove the used aqueous pack agent from the skin surface. In order to easily attract and remove the aqueous pack agent from the skin surface, the content of the magnetic powder is preferably 15 mass % or more, more preferably 30 mass % or more and further preferably 50 mass % or more.

In contrast, if the content of the magnetic powder exceeds 80 mass %, since the contents of water and a thickener become insufficient, the aqueous pack agent may be formed into a sticky mass. Because of this, it is difficult to spread the aqueous pack agent over the skin. Thus, in order to obtain the aqueous pack agent in a paste-like appearance suitable for application to the skin, the content of the magnetic powder is preferably 80 mass % or less, more preferably 75 mass % or less and further preferably 70 mass % or less.

The viscosity of the aqueous pack agent is preferably 9000 mPa·s or more. In this case, the dispersed state of the magnetic powder in the aqueous pack agent can be maintained for a longer time. Accordingly, the state where a sufficient amount of magnetic powder for attraction and removal is contained in the aqueous pack agent applied to the skin surface can be more easily realized. As a result, the magnetic powder and the used aqueous pack agent can be easily attracted and removed from the skin surface, and the used aqueous pack agent and fine particles in the magnetic powder are more suppressed from remaining on the skin surface.

The aqueous pack agent may contain a thixotropic agent for imparting thixotropy. The aqueous pack agent having thixotropy has a high viscosity in the state where the aqueous pack agent does not flow during e.g., storage. Whereas, in the state where the pack agent flows during e.g., application of the agent to the skin, the viscosity of the aqueous pack agent decreases. Accordingly, in the aqueous pack agent containing a thixotropic agent, precipitation of the magnetic powder can be prevented when the aqueous pack agent is in storage. In contrast, when applied to the skin, the aqueous pack agent is likely to have a suitable viscosity for application. As a result, the aqueous pack agent is suitably applied to the skin while preventing precipitation of a magnetic powder.

As the thixotropic agent, a conventional thixotropic agent for use in cosmetics, such as bentonite, 12-hydroxystearic acid and crystalline cellulose, is used.

The aqueous pack agent may contain a surfactant. The surfactant has an action of dispersing a magnetic powder in the aqueous pack agent. Accordingly, in the aqueous pack agent containing a surfactant, the state where the magnetic powder is dispersed can be more reliably realized. As a result, the aqueous pack agent provides a smooth paste-like appearance and the user feels smoother spreading over the skin.

As the surfactant, a conventional surfactant for use in cosmetics can be used. Examples of the surfactant include PEG-7 glyceryl cocoate, polyglyceryl-10 laurate, an alkyl sulfate, an acylamino acid salt, a polyoxyethylene alkyl ether sulfate, an alkyl ether phosphate, an alkyl polyethylene glycol ether, a glycerol polypropylene glycol ether, an alkyl polyglycerol ether and an ethylene oxide-propylene oxide block copolymer. These surfactants may be used alone or in combination.

The aqueous pack agent may further contain a beauty component providing a beauty effect on the skin, other than the aforementioned components. As described above, the aqueous pack agent rarely forms an oil film on the skin surface after the used aqueous pack agent is attracted and removed. Thus, the amount of a substance which inhibits the infiltration of a beauty component, such as dirt of the skin, waste or an oil film is low on the skin surface after the aqueous pack agent is attracted and removed. In this state, a beauty component easily infiltrates. The beauty component, which is blended in advance in the aqueous pack agent, can remain applied onto the skin surface even though the aqueous pack agent is attracted and removed from the skin surface. Accordingly, the beauty component more easily infiltrates into the skin surface and a more excellent beauty effect is easily obtained.

Examples of the beauty component to be used herein include a whitening component such as an ascorbic acid derivative, kojic acid, arbutin and tranexamic acid; a nutritional component such as an amino acid, a vitamin, a plant extract and a microbially fermented product; and a moisturizing component.

The aqueous pack agent may contain additives usually used in cosmetics other than the aforementioned components. Examples of the additives include a lubricant, an anti-microbial agent, a fragrance and a pH adjusting agent. These additives can be appropriately added as long as the effects of the present invention are not undermined.

It is preferable that the aqueous pack agent has an electrical conductivity of 20 µS/cm or more at 25° C. In this case, since a weak current for facilitating infiltration of an iontophoresis component into the skin easily flows, iontophoresis can be easily performed.

As the magnetic powder to be contained in the aqueous pack agent, a magnetic powder constituted of a ferromagnetic material is used. When the magnetic powder comes into direct contact with e.g., water contained in the aqueous pack agent, the magnetic powder is oxidized and rust may be formed. The magnetic powder oxidized to the extent that rust is produced, is hardly attracted and removed from the skin since the magnetic property of the powder deteriorates. Also, rust of the magnetic powder is not preferable in blending with an aqueous pack agent in view of appearance. Accordingly, it is preferable to use a magnetic power capable of suppressing formation of rust for a long period of time.

For example, the magnetic powder is constituted of a ferromagnetic metal and an oxidation resistant film may be formed on the surface of each particles constituting the magnetic powder. In this case, sufficiently large magnetic force can be applied to the whole magnetic powder by a ferromagnetic metal when a magnet or the like is allowed to approach. Accordingly, the magnetic powder can be easily attracted and removed from the skin surface together with the used aqueous pack agent.

Owing to the presence of the oxidation resistant film, it is possible to suppress direct contact of the particles with a material that may serve as an oxidation agent, such as water, contained in the aqueous pack agent. Consequently, rust formation of the magnetic powder can be suppressed for a long period of time. As the result of suppressing the contact between the particles and e.g., water, the magnetic powder is rarely oxidized and the magnetic property can be maintained for a long period of time.

As mentioned above, the magnetic powder constituted of a ferromagnetic metal and having an oxidation resistant film can maintain excellent magnetic property for a long period of time. Accordingly, an aqueous pack agent containing the magnetic powder can maintain its performance for a long period of time.

As the aforementioned ferromagnetic metal, for example, a single metal such as iron, nickel and cobalt, and an alloy containing at least one of these metal elements are mentioned. Note that these single metals and alloys may usually contain other chemical components such as inevitable impurities.

As the oxidation resistant film, a wide variety of materials can be employed as long as they suppress direct contact between the particles and e.g., water. Examples of the oxidation resistant film that can be used include an inorganic coating film, a fatty acid coating film, a silane coating film and a resin coating film. The inorganic coating film can be formed by subjecting the magnetic particle to a treatment with a phosphate salt such as iron phosphate, zinc phosphate, calcium phosphate and manganese phosphate.

The fatty acid coating film may contain a structure derived from a fatty acid such as lauric acid, myristic acid, stearic acid, palmitic acid, oleic acid and linoleic acid. The fatty acid coating film can be formed by subjecting the magnetic powder to a surface treatment with a solution containing a fatty acid.

The silane coating film may contain a structure derived from an alkylalkoxysilane such as methyltrimethoxysilane, dimethyldimethoxysilane, trimethylmethoxysilane, methyltriethoxysilane, methyltriphenoxysilane, ethyltrimethoxysilane, n-propyltrimethoxysilane, diisopropyldimethoxysilane and isobutyltrimethoxysilane. The silane coating film can be formed by treating the surface of the magnetic powder with an alkoxysilane.

Examples of the resin constituting a resin coating film that can be used include a resin such as an acrylates copolymer, a polyvinyl alcohol, a polyvinyl pyrrolidone, a methoxy ethylene-maleic anhydride copolymer, a cationic cellulose, a polyacrylic acid ester copolymer, a methacrylic acid ester copolymer, an epoxy resin and a silicone resin. The resin coating film can be formed by applying a resin as mentioned above to the surface of the magnetic powder.

The magnetic powder may contain a ferromagnetic ferrite as a main component. The "main component" herein refers to a chemical component contained in the largest amount. The magnetic powder usually contains, other than a ferromagnetic ferrite serving as a main component, e.g., an iron-based oxide such as wustite and hematite each having a different degree of oxidation, and inevitable impurities.

A ferrite is low in variation of magnetic property and color tone. Accordingly, an aqueous pack agent containing the magnetic powder having a ferrite as a main component can be reduced in variation in ease of attraction and removal and color tone. In addition, since a ferrite is an iron oxide, further oxidization of the magnetic powder rarely takes place in an aqueous pack agent. For the reason, even if the aqueous pack agent is stored for a long term, e.g., magnetic property of the magnetic powder rarely changes and performance can be maintained for a long term.

A magnetic powder having a ferrite as a main component may have an oxidation resistant film on the surface. In this case, owing to the presence of the oxidation resistant film, the magnetic powder is more rarely oxidized. Thus, the aqueous pack agent can maintain performance for a long period of time.

Examples of the ferromagnetic ferrite include a spinel ferrite, a magneto-plumbite ferrite, a garnet ferrite, a perovskite ferrite and so on. Of these ferrites, a soft ferrite high in saturation magnetization and low in both residual magnetization and magnetic coercive force is preferably contained as a main component of the magnetic powder. Examples of the soft ferrite include a spinel ferrite having a formula represented by $(MO)_x(Fe_2O_3)_y$ (where x+y=100 mol %, M is one or two or more metal elements selected from metallic elements e.g., Fe, Mn, Mg, Sr, Ca, Ba, Cu, Zn, Ni, Li and Co). Of the spinel ferrites, a ferrite having high saturation magnetization is preferably used.

In the magnetic powder to be used in the aqueous pack agent, the number of the elements constituting a ferrite serving as a main component is preferably small. Thus, magnetite ($Fe_3O_4$) having high saturation magnetization and constituted of two elements, Fe and O, is further preferably contained as a main component of the magnetic powder.

It is preferable that the magnetic powder has a chemical component consisting of 80 mass % or more of magnetite and the balance being wustite, hematite and inevitable impurities. In this case, the ratio of a diamagnetic material in the magnetic powder decreases, and thus the magnetic force acting on the whole magnetic powder increases. As a result, the aqueous pack agent can be more efficiently attracted and removed. Since the degree of oxidation of wustite is low compared to e.g., magnetite, if the content of wustite is reduced, it is likely to avoid further oxidation of the magnetic powder. Consequently, the performance of the aqueous pack agent can be stabilized for a long term.

The mean volume particle diameter of a magnetic powder is preferably 20 to 150 μm and more preferably 50 to 75 μm. In this case, it is possible to easily attract and remove the used aqueous pack agent from the skin surface. The mean volume particle diameter of the magnetic powder can be calculated in terms of 50% cumulative particle diameter (median diameter) obtained in the volume distribution mode in under-sieve representation of the particle size distribution obtained by the laser diffraction scattering method.

If the mean volume particle diameter is less than 20 μm, the particle size distribution of the magnetic powder tends to have a distribution pattern in which the content of an excessively small particle size is large. The magnetic force acting on each of the particles decreases as the size of the particle reduces. Because of this, particles having an excessively small particle diameter are difficult to be attracted by a magnet or the like and tend to remain on the skin surface. Also in this case, the magnetic force acting on the whole magnetic powder becomes weak, with the result that the used aqueous pack agent is likely to remain on the skin surface.

In contrast, if the mean volume particle diameter exceeds 150 μm, the particle size distribution has a distribution pattern in which the content of an excessively large particle diameter is large. In this case, the user feels rough when the aqueous pack agent containing the magnetic powder is used. Likewise, the sense of use may deteriorate.

As mentioned above, the aqueous pack agent having a magnetic powder in which the mean volume particle diameter is controlled to fall within 20 to 150 μm provides an excellent sense of use because fine particles contained in the magnetic powder and the used aqueous pack agent are suppressed from remaining on the skin surface.

The magnetic powder preferably has a mean volume particle diameter being 50 to 75 μm as determined from a particle size distribution obtained by a laser diffraction scattering method, a content of particles with a particle diameter being less than 37 μm of 15 mass % or less, and a content of particles with a particle diameter being 105 μm or more of 5 mass % or less.

The content of particles having a particle diameter being less than 37 μm (hereinafter sometimes referred to as "small-diameter particles") can be measured in terms of, for example, the amount of particles that can pass through a standard sieve having a nominal size of 37 μm (400 meshes).

The content of particles having a particle diameter being 105 μm or more (hereinafter sometimes referred to as "large-diameter particles") can be measured in terms of, for example, the amount of particles that cannot pass through a standard sieve having a nominal size of 105 μm (145 meshes).

As described above, in order to obtain the aqueous pack agent rarely remaining on the skin surface and providing smooth application to the skin, it is preferable that the particle size distribution of the magnetic powder has a distribution pattern in which the content of particles having an excessively small particle diameter and the content of particles having excessively large particle diameter are both small. In other words, the mean volume particle diameter of the magnetic powder is more preferably 50 to 75 µm.

However, it is difficult to reliably reduce the content of particles having an excessively small particle diameter only by controlling the mean volume particle diameter to fall within the range of 50 µm or more. Thus, it is important not only to control the mean volume particle diameter to fall within the range of 50 µm or more but also to regulate the content of small-diameter particles to be 15 mass % or less as mentioned above. The content of particles having an excessively small particle diameter can be certainly reduced by regulating the content of small-diameter particles to fall within the range of 15 mass % or less.

Similarly, it is difficult to reliably reduce the content of particles having an excessively large particle diameter only by controlling the mean volume particle diameter to fall within the range of 75 µm or less. Thus, it is important not only to control the mean volume particle diameter to fall within the range of 75 µm or less but also to regulate the content of large-diameter particles to be 5 mass % or less as mentioned above. The content of particles having an excessively large particle diameter can be certainly reduced by regulating the content of large-diameter particles to fall within the range of 5 mass % or less.

As mentioned above, the most suitable particle-size distribution in which the content of particles having an optimal diameter is large can be realized not only by controlling the mean volume particle diameter of the magnetic powder to fall within a specific range mentioned above but also by regulating both the content of small-diameter particles and the content of large-diameter particles. The magnetic powder, which is finely and carefully controlled so as to have a particle size distribution as mentioned above, exhibits the most suitable properties as the magnetic powder to be blended in an aqueous pack agent. Accordingly, the aqueous pack agent containing such the magnetic powder more rarely remains on the skin surface and provides a smoother application to the skin.

The magnetic powder preferably has a saturation magnetization of 80 $Am^2/kg$ or more. In this case, the magnetization of the magnetic powder can be sufficiently increased and the magnetic force acting on the whole magnetic powder can be further increased. As a result, the used aqueous pack agent can be easily attracted and removed from the skin surface and can be prevented from remaining on the skin surface.

EXAMPLE

Example 1

Figure 2:
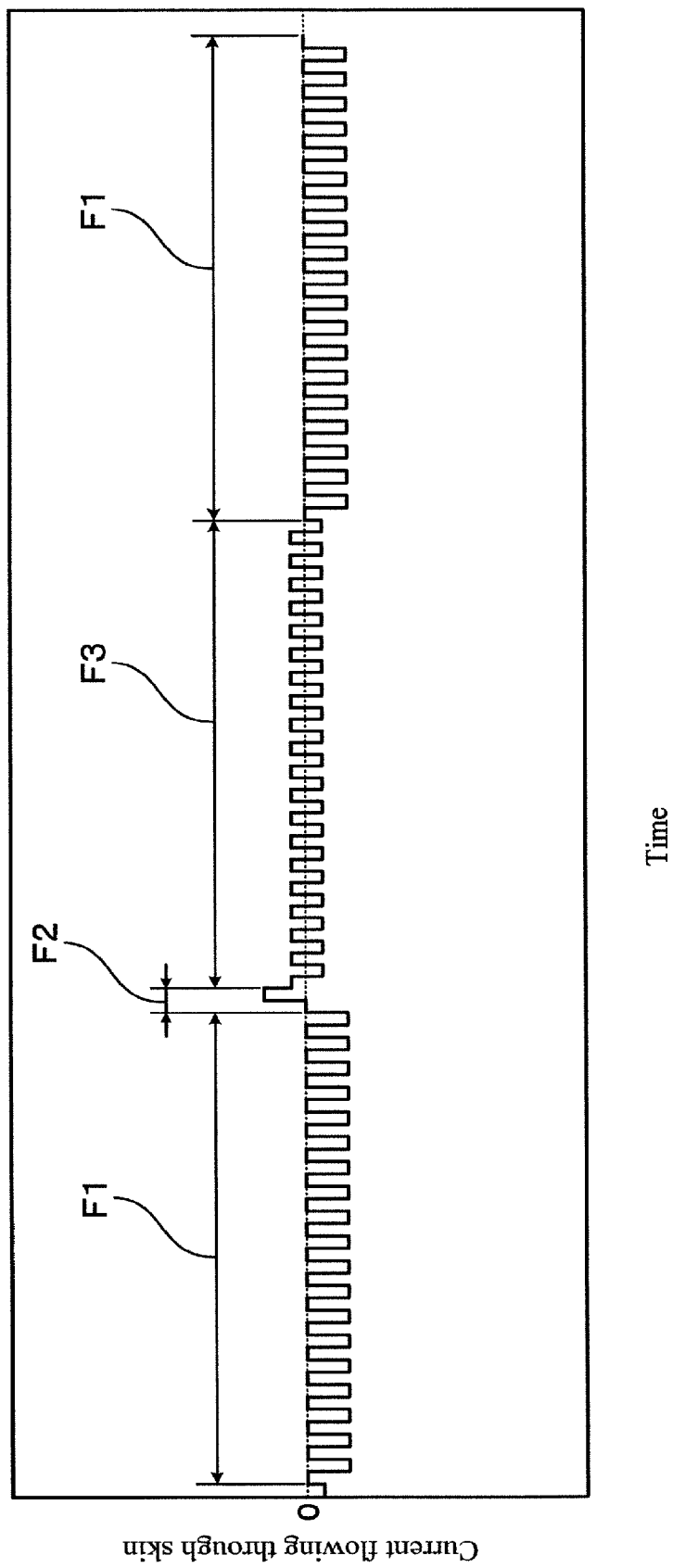
FIG. 2 shows a waveform chart of an iontophoretic current in Example 1.
Figure 3:
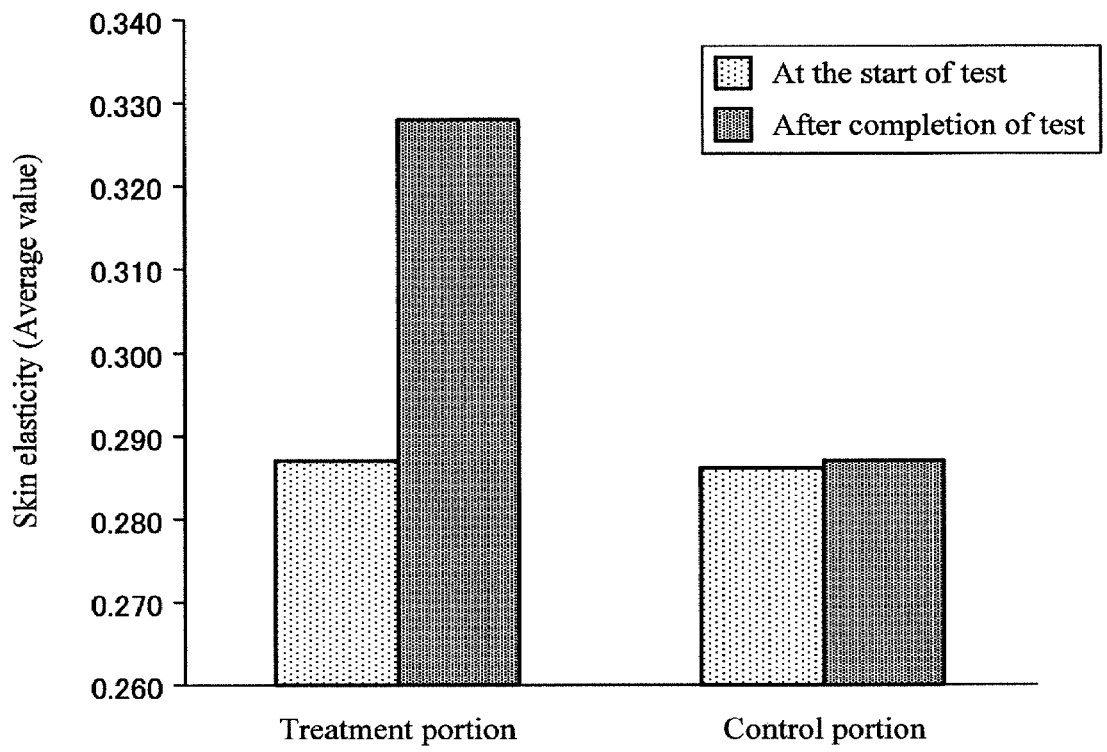
FIG. 3 is a graph showing a change in skin elasticity before and after the test in Example 1.

Referring to FIG. 1 to FIG. 3, examples of the beauty care method will be explained. In the beauty care method of this example, first, a step of applying an aqueous pack agent 1, which comprises a water, a magnetic powder 11 containing a ferromagnetic ferrite as a main component, a thickener and a charged iontophoretic component 13, to the skin 2 (FIG. 1 (a)) is carried out. Then, a step of applying magnetic force to the magnetic powder 11 contained in the aqueous pack agent 1 applied to the skin 2 and attracting and removing the magnetic powder 11 from the skin surface 21 by the magnetic force while leaving an aqueous solution 12 of the iontophoretic component 13 on the skin surface 21 (FIG. 1 (b)) is carried out. Thereafter, a step of applying an iontophoretic current to the skin 2, on which the aqueous solution 12 is placed, to allow the iontophoretic component 13 to infiltrate into the skin 2 (FIG. 1 (c)) is carried out. The beauty care method will be more specifically described below.

In the step of applying the aqueous pack agent 1 to the skin 2, the aqueous pack agent 1 is applied to the entire surface of a desired part at which a beauty effect is to be provided. The aqueous pack agent 1 is preferably applied with a thickness through which the color of the skin 2 cannot be seen. Note that, a detailed composition of the aqueous pack agent 1 will be described later.

In the step of attracting and removing the magnetic powder 11, a magnet 3 is allowed to approach the aqueous pack agent 1 applied to the skin 2, as shown in FIG. 1 (b). In this manner, the magnetic powder 11 is attracted by the magnet 3 and removed from the skin surface 21 by the magnetic force. Simultaneously with the magnetic powder 11, a used aqueous pack agent 100 and dirt 200 of the skin 2 and others attached to the magnetic powder 11 are attracted and removed from the skin surface 21 by the magnetic force. The magnet 3 used in this step may be a permanent magnet such as a ferrite magnet and a neodymium magnet or an electromagnet.

In contrast, an aqueous solution 12 containing the iontophoretic component 13 is not attracted and removed together with the used aqueous pack agent 100 and others and remains on the skin surface 21. In this manner, the aqueous pack agent 1 is attracted and removed from the skin surface 21; at the same time, the aqueous solution 12 containing the ionized iontophoretic component 13 remains applied to the skin surface 21, as shown in FIG. 1 (b).

In the step of introducing the iontophoretic component 13 into the skin 2, as shown in FIG. 1 (c), a working electrode 41 is allowed to be contact with the skin surface 21 on which the aqueous solution 12 containing the iontophoretic component 13 is applied; whereas, a counter electrode 42 is allowed to be in contact with the skin surface 211 where the aqueous solution 12 is not applied. In this state, a voltage is applied between the working electrode 41 and the counter electrode 42 to supply an iontophoretic current to the skin 2. Note that, the iontophoretic component 13 used in this example is sodium L-ascorbic acid-2-phosphate. Sodium L-ascorbic acid-2-phosphate is ionized into an L-ascorbic acid 2-phosphate ion 131 and a sodium ion in the aqueous solution 12. Then, an anion, i.e., L-ascorbic acid 2-phosphate ion 131, is allowed to infiltrate into the skin by iontophoresis. Owing to this, beauty effects such as improvement of elasticity, wrinkles and age spots of skin and shrinkage of pores can be expected.

The iontophoretic current of this example is constituted of sequential repeats of an iontophoresis step of supplying an iontophoretic current (basic waveform F1) having a single-polarity to the contact portion between the working electrode 41 and the skin 2; a reset pulse step of supplying a pulse current (basic waveform F2) having the other polarity to the contact portion; and a skin care step of supplying a current (basic waveform F3) in which polarity is alternately changed, to the contact portion, as shown in FIG. 2.

In the iontophoresis step, a pulse voltage is applied between the working electrode 41 and the counter electrode 42 in a plurality of times while controlling the potential difference between the electrodes such that the electrical potential of the working electrode 41 is lower than that of the counter electrode 42. Owing to this, the iontophoretic current becomes a negative pulse current as shown in basic waveform F1 of FIG. 2. The iontophoretic current flows through the skin 2 and infiltration of L-ascorbic acid 2-phosphate ion 131 into the skin is facilitated.

In the reset pulse step, a pulse voltage is applied once between the working electrode 41 and the counter electrode 42 while controlling the potential difference between the two electrodes such that the electrical potential of the working electrode 41 is higher than that of the counter electrode 42. Owing to this, a positive pulse current flows through the skin 2, as shown in basic waveform F2 of FIG. 2. The reset pulse step is carried out in this manner to neutralize the bias in charge produced in the skin 2 in the iontophoresis step.

In the skin care step, a square wave, in which the high and low of the potential difference between the working electrode 41 and the counter electrode 42 alternately change, is applied to the both electrodes. Consequently, a square wave current, in which a positive polarity and negative polarity alternately change, as shown in basic waveform F3 of FIG. 2, flows through the skin 2. As mentioned above, if a weak current in which polarity alternately changes flows through the skin 2, effects such as vitalization of skin cells, improvement of lymph flow, improvement of blood circulation and improvement of metabolism, can be exerted. Accordingly, it is expected to obtain beauty effects such as improvement of elasticity of the skin 2 and beautifying the skin 2, by performing the skin care step.

In this example, the beauty effect of the skin 2 obtained by the beauty care method was evaluated. The evaluation contents and evaluation results will be described below.

<Test Subject>

Test subjects were eight Japanese women of 20 or more and less than 60 years old.

<Test Conditions>

[Aqueous Pack Agent 1]

Specific composition of the aqueous pack agent 1 to be applied to the skin 2 is as follows:

| | |
|---|---|
| Water | 7.92 mass % |
| Magnetic powder 11 | 65 mass % |
| Thickener | |
| Glycerin | 17.5 mass % |
| Sodium polyacrylate | 0.01 mass % |
| Surfactant | |
| Polyglyceryl monolaurate | 0.2 mass % |
| Iontophoretic component 13 | |
| Sodium L-ascorbic acid-2-phosphate | 0.1 mass % |
| Lubricant, pH adjusting agent, preservative and etc. | balance |

[Magnetic Powder 11]

A method for manufacturing the magnetic powder 11 used in the aqueous pack agent 1 and properties of the magnetic powder 11 are as follows:

Manufacturing Method

A slurry was prepared by adding a water to a hematite ($Fe_2O_3$) powder so as to have a solid content of 55 mass %. Subsequently, 1 mass % of a polyvinyl alcohol relative to the solid content of the slurry, 0.9 mass % of a carbon black and 0.5 mass % of a polycarboxylate salt were added to the resultant slurry. Thereafter, a water was added to the mixture to prepare a slurry having 55 mass % of a solid content. Then, the resultant slurry was stirred by use of an attritor for one hour, and then, spherically granulated by use of a spray dryer. The grain sizes of the granules obtained were controlled by a gyro shifter.

The spherical granules controlled in grain size were heated at 1320° C. for 3 hours to reduce a raw-material hematite. In this manner, a calcined product containing magnetite as a main component was obtained. Note that, the granules was heated by use of a tunnel type electric furnace in a nitrogen atmosphere.

The resultant calcined product was pulverized and classified by use of a gyro shifter in combination with an air classifier. In this manner, a particle size distribution was controlled. Thereafter, particles having a large magnetic susceptibility were selected by electromagnetic separation to obtain the magnetic powder 11.

By performing surface treatment to the resultant magnetic powder 11 as mentioned above, a resin film consisting of an acrylates copolymer was formed on the surface of particles constituting the magnetic powder 11.

Mean Volume Particle Diameter

The mean volume particle diameter was calculated by the following method. First, a 0.2% aqueous solution of sodium hexametaphosphate was added to the magnetic powder 11. The resultant mixture was subjected to an ultrasonic treatment using an ultrasonic homogenizer (UH-3C, manufactured by Ultrasonic Engineering Co., Ltd.) for one minute to prepare a dispersion liquid of the magnetic powder 11. The dispersion liquid was introduced in a micro track particle-size analyzer (Model 9320-X100 manufactured by Nikkiso Co., Ltd.). Analysis was performed in the conditions: a refractive index of 1.81, a temperature of 25±5° C., and a humidity of 55±15%, to obtain a particle size distribution in accordance with the laser diffraction scattering method. From the resultant particle size distribution, a cumulative 50% particle diameter represented in terms of mesh size of sieves with a volume distribution mode, was calculated and employed as a mean volume particle diameter (median diameter).

From the above results, the mean volume particle diameter of the magnetic powder 11 was about 70 μm.

Contents of Small-diameter Particles and Large-diameter Particles

The magnetic powder 11 was classified by a method according to JIS H 2601 using the standard sieves specified in JIS Z 8801. In this way, the content of small-diameter particles, namely, particles passed through the standard sieve having a nominal dimension of 37 μm (400 meshes) and the content of large-diameter particles, namely, particles not passed through a standard sieve having a nominal dimension of 105 μm (145 meshes) were measured.

As a result, the content of the small-diameter particles in the magnetic powder 11 was 6.7 mass % and the content of the large-diameter particles was 0 mass %.

Saturation Magnetization, Residual Magnetization and Magnetic Coercive Force

Magnetic properties were measured by use of an integral type B-H tracer (Model: BHU-60, manufactured by Riken Denshi Co., Ltd.) in the following procedure. First, an H coil for measuring a magnetic field and a 4πI coil for measuring magnetization were placed between electromagnets and the magnetic powder 11 was put in the 4πI coil. Then, the current values of the electromagnets were changed to vary the magnetic field H. The outputs from the H coil and the 4πI coil were separately integrated. The output from H coil was plotted on the X-axis and the output from the 4πI coil was plotted on the Y-axis. In this manner, a hysteresis loop was drawn on a recording paper. From the hysteresis loop, saturation magnetization, residual magnetization and magnetic coercive force were calculated. Note that, the measurement condition for the hysteresis loop were as follows: sample amount of about 1 g, sample cell of 7 mmφ±0.02 mm in inner diameter and 10 mm±0.1 mm in height, the number of turns of 4πI coil of 30; applied magnetic field of 3000 oersteds.

As a result, the magnetic powder 11 had a saturation magnetization of 82 $Am^2$/kg, a residual magnetization of 82 $Am^2$/kg and a magnetic coercive force of 24 Oe.

Chemical Components

The composition ratio of magnetite ($Fe_3O_4$), hematite ($Fe_2O_3$) and wustite (FeO) was calculated in accordance with the following method using the X-ray diffraction method.

As a measuring device, "X'PertPRO MPD" manufactured by PANalytical B.V. was used. Measurement was performed using a Co bulb (CoKα beam) as an X-ray source, a centralized optical system as an optical system and a fast detector, "X'Celarator", by continuous scanning at a rate of 0.2°/sec. The measurement results were analyzed by analysis software, "X'PertHighScore" in the same manner as in ordinary crystal structure analysis of a powder to identify a crystal structure. Thereafter, an abundance ratio on a weight basis was calculated by refinement of the obtained crystal structure. Note that, when the abundance ratio of magnetite, hematite and wustite was calculated, Fe and O were regarded as essential elements.

As the X-ray source to be used in the X-ray diffraction measurement, a Cu bulb may be used without a problem; however, in the case of a Fe-rich sample, the background noise becomes large compared to a peak of a measuring target. Thus, a Co bulb is preferably used. Even if collimating optics is used as the optical system, the same results can be obtained; however, X-ray intensity is low and a long time is required for measurement. For this reason, measurement in a centralized optical system is preferable. The speed of the continuous scanning is not particularly limited; however, the intensity of the main peak of magnetite, i.e., the peak in the (311) plane, became 50000 cps or more in order to obtain a sufficient S/N ratio for analyzing a crystal structure. A sample was set in a sample cell such that particles were not preferentially oriented in a specific direction. In this manner, measurement was performed.

As a result, the magnetic powder 11 contained a chemical component having 89.7 mass % of magnetite, 4.1 mass % of hematite and 6.2 mass % of wustite.

<Test Method>

The right half of the face of a subject was used as a treatment portion and a treatment was applied to the treatment portion once every three days in accordance with the following method. First, cleansing and face-wash were performed. Thereafter, the aqueous pack agent 1 was applied only to the treatment portion and the treatment portion was allowed to leave for three minutes. Three minutes later, the magnet 3 was allowed to approach the aqueous pack agent 1 applied to the skin 2, and the magnetic powder 11 and the used aqueous pack agent 1 were attracted and removed from the skin 2. After the attraction and removal, the iontophoretic current shown in FIG. 2 was applied to the treatment portion for about 5 minutes. In this manner, the treatment was completed.

Note that, the left half of the face of each subject was used as a control portion and treated in accordance with the following procedure.

After cleansing and face-wash, an oily pack agent containing 65 mass % of the magnetic powder 11 was applied to the control portion and allowed to leave for 3 minutes. Three minutes later, the magnet 3 was allowed to approach the oily pack agent applied to the skin 2 and the magnetic powder 11 and the used oily pack agent were attracted and removed from the skin 2. After the attraction and removal, a lotion containing sodium L-ascorbic acid-2-phosphate was applied to the control portion and the iontophoretic current was applied similarly to the treatment portion for about 5 minutes.

Note that, specific compositions of the oily pack agent and lotion applied to the control portion are as follows:

[Oily Pack Agent]

| Excipient | |
|---|---|
| Triethylhexanoin | 21.4 mass % |
| Vaseline | 3.5 mass % |
| Magnetic powder 11 | 65 mass % |
| Surfactant | |
| Glyceryl stearate | 1.1 mass % |
| Polyglyceryl Laurate-10 | 0.7 mass % |
| Emulsifier | |
| Cetanol | 1.8 mass % |
| Sorbitan Stearate | 1.8 mass % |
| Lubricant, preservative and others | balance |

[Lotion]

| Iontophoretic component 13 | |
|---|---|
| Sodium L-ascorbic acid-2-phosphate | 0.1 mass % |
| Sodium citrate | 0.08 mass % |
| Citric acid | 0.02 mass % |
| Butylene glycol | 5 mass % |
| Glycerin | 3 mass % |
| Dipropylene glycol | 2 mass % |
| Water, thickener, preservative and etc. | balance |

<Evaluation>

At the starting time of the test and the completion time of the test (after a lapse of 4 weeks), skin elasticity was measured by a skin viscoelasticity measuring device ("Cutometer (registered trade mark)", manufactured by Courage+Khazaka). Measurement was repeated 5 times with respect to each of the treatment portion of the cheek and the control portion of the cheek and 5 measurement values were averaged. Note that, skin elasticity was measured after the measurement sites were acclimated to an environment of temperature of 22±2° C., relative humidity of 50±3% RH by exposing the sites to the environment continuously for 10 minutes.

Table 1 shows skin elasticity values at the starting time of the test and the completion time of the test, and the difference between the skin elasticity values per subject. FIG. 3 is a graph showing the average skin elasticity value of the subjects at the starting time of the test and the average skin elasticity value of the subjects at the completion time of the test. The vertical axis in FIG. 3 represents the average skin elasticity value.

As is apparent from Table 1 and FIG. 3, the skin elasticity of the treatment portion was improved after the test in almost all subjects. Furthermore, it was demonstrated that skin elasticity tends to be improved with the passage of time. The skin elasticity at the completion time of the test was improved by 14.5% in average, compared to the skin elasticity at the starting time of the test. An increase of the skin elasticity is statistically significant at a 1% level.

In contrast, the skin elasticity of the control portion was improved only in half of the subjects; however, tendency of improving skin elasticity with time was not observed. The skin elasticity at the completion time of the test increased by 0.4% in average, compared to the skin elasticity at the starting time of the test. However, it was not recognized that the increase in skin elasticity value has a statistically significant difference. From the above results, it is found that beauty effect, i.e., improvement of skin elasticity, was obtained by the beauty care method.

TABLE 1

| | Treatment Portion | | | Control Portion | | |
|---|---|---|---|---|---|---|
| Test Subject ID | At the Start of Test | After Completion of Test | Difference between Skin Elasticity Values | At the Start of Test | After Completion of Test | Difference between Skin Elasticity Values |
| 1 | 0.272 | 0.340 | 0.068 | 0.282 | 0.278 | −0.004 |
| 2 | 0.286 | 0.298 | 0.012 | 0.317 | 0.272 | −0.045 |
| 3 | 0.302 | 0.320 | 0.018 | 0.284 | 0.292 | 0.008 |
| 4 | 0.262 | 0.312 | 0.050 | 0.296 | 0.230 | −0.066 |
| 5 | 0.298 | 0.384 | 0.086 | 0.290 | 0.356 | 0.066 |
| 6 | 0.290 | 0.338 | 0.048 | 0.284 | 0.256 | −0.028 |
| 7 | 0.268 | 0.326 | 0.058 | 0.246 | 0.272 | 0.026 |
| 8 | 0.314 | 0.306 | −0.008 | 0.288 | 0.340 | 0.052 |
| Average Value | 0.287 | 0.328 | 0.042 | 0.286 | 0.287 | 0.001 |

Example 2

Figure 4:
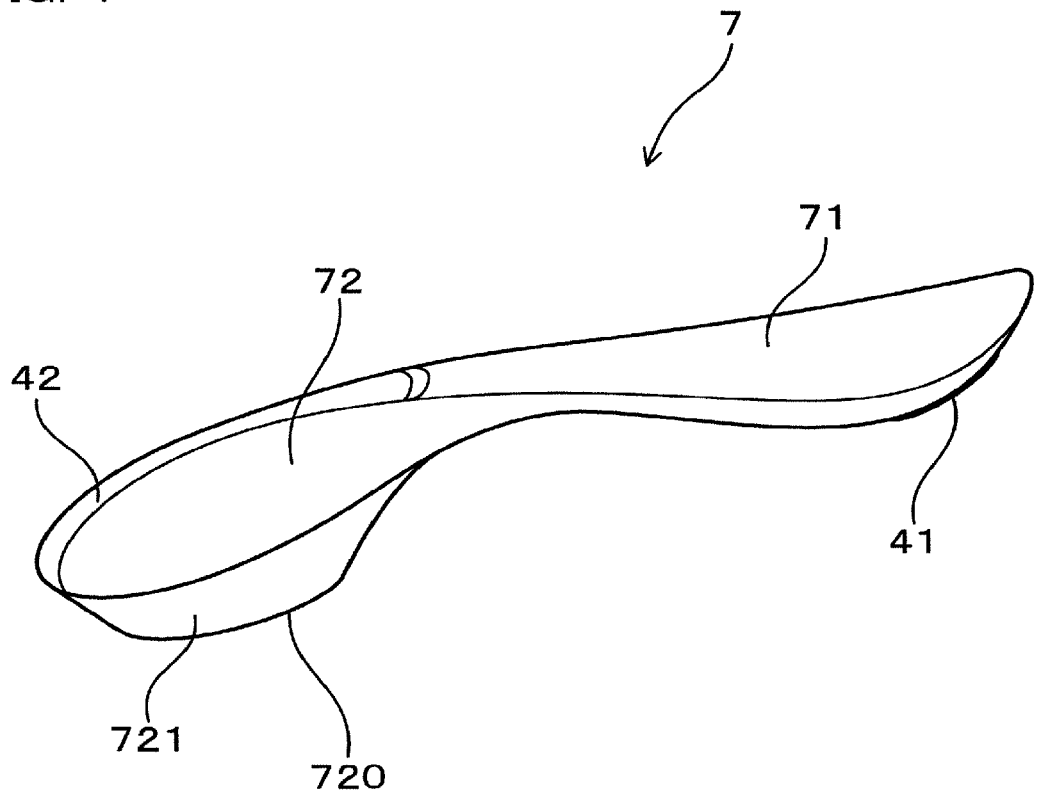
FIG. 4 is a perspective view of the beauty care instrument described in Example 2.
Figure 5:
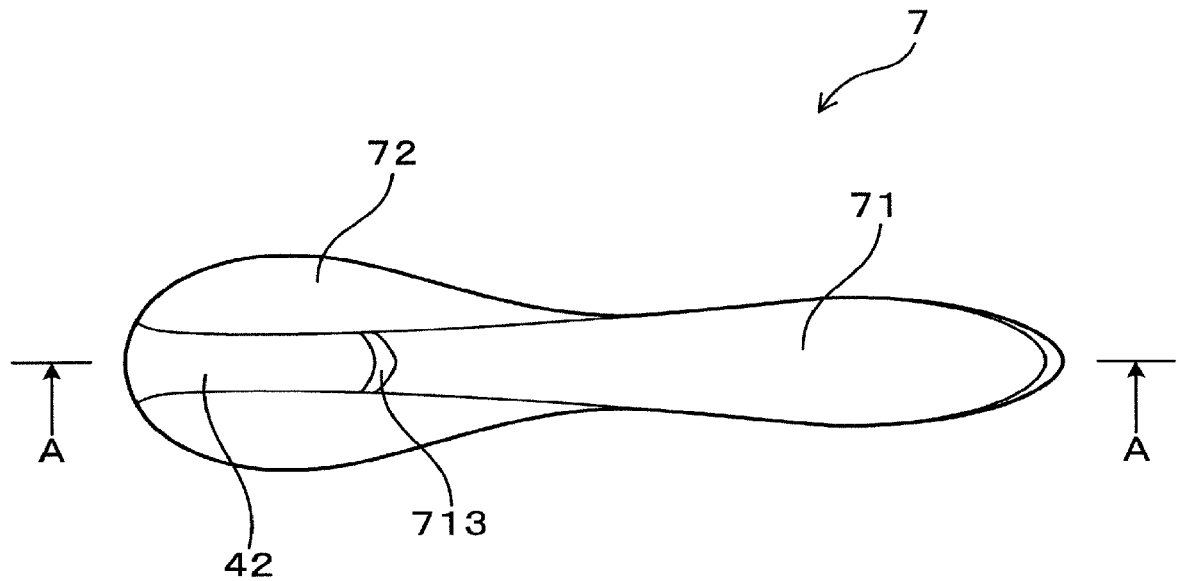
FIG. 5 is a plan view of the beauty care instrument described in Example 2, as viewed from the top, i.e., an opposite side to the magnetic force generation surface.
Figure 6:
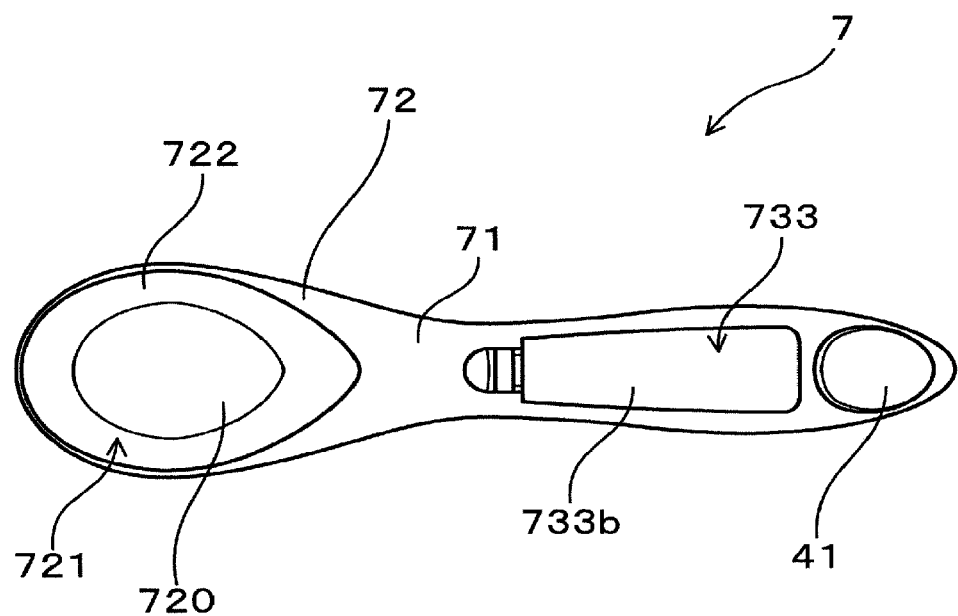
FIG. 6 is a plan view of the beauty care instrument described in Example 2, as viewed from the bottom, i.e., the magnetic force generation surface.
Figure 7:
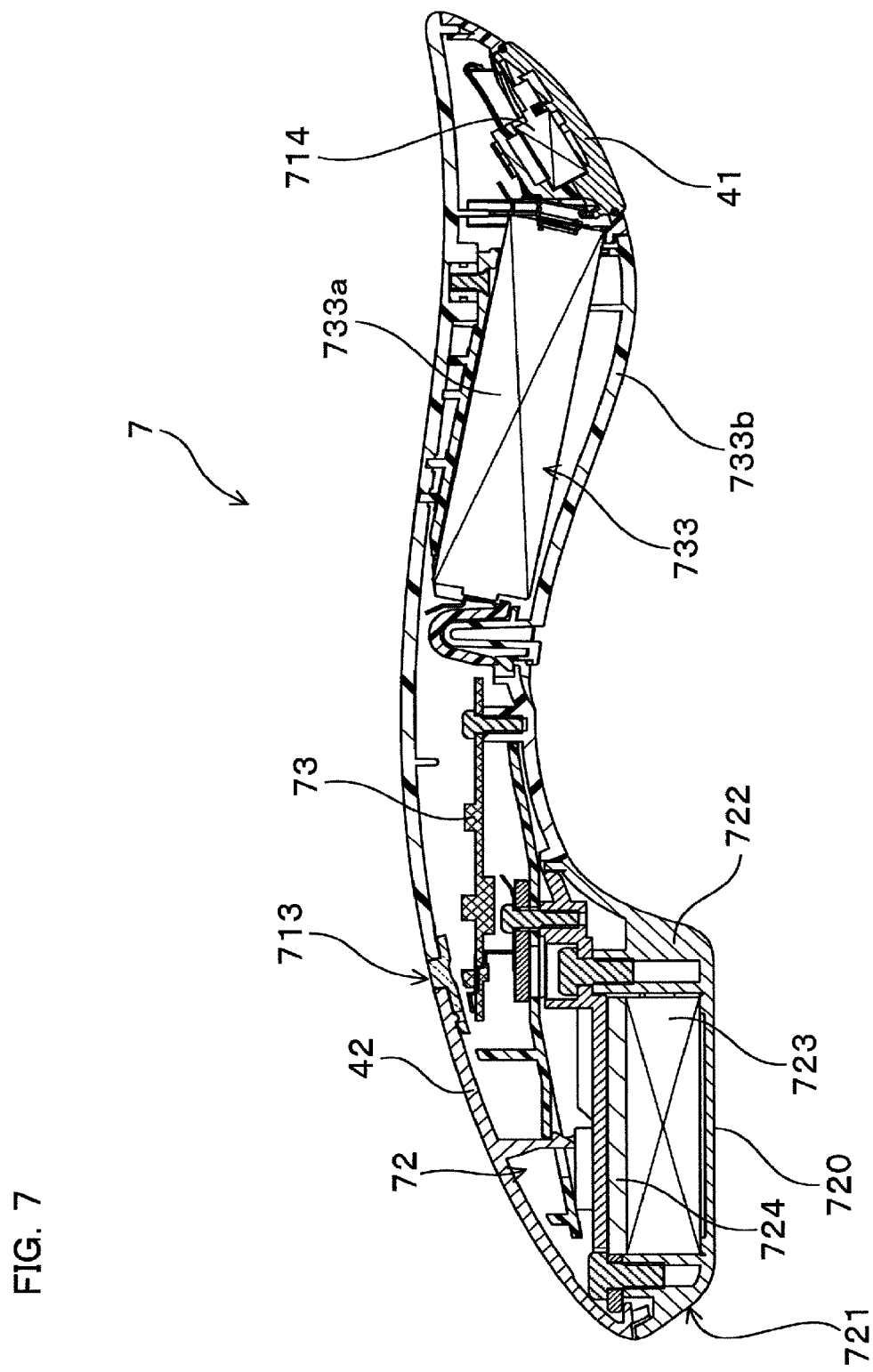
FIG. 7 is a sectional view along the line defined by A-A of FIG. 5.
Figure 11:
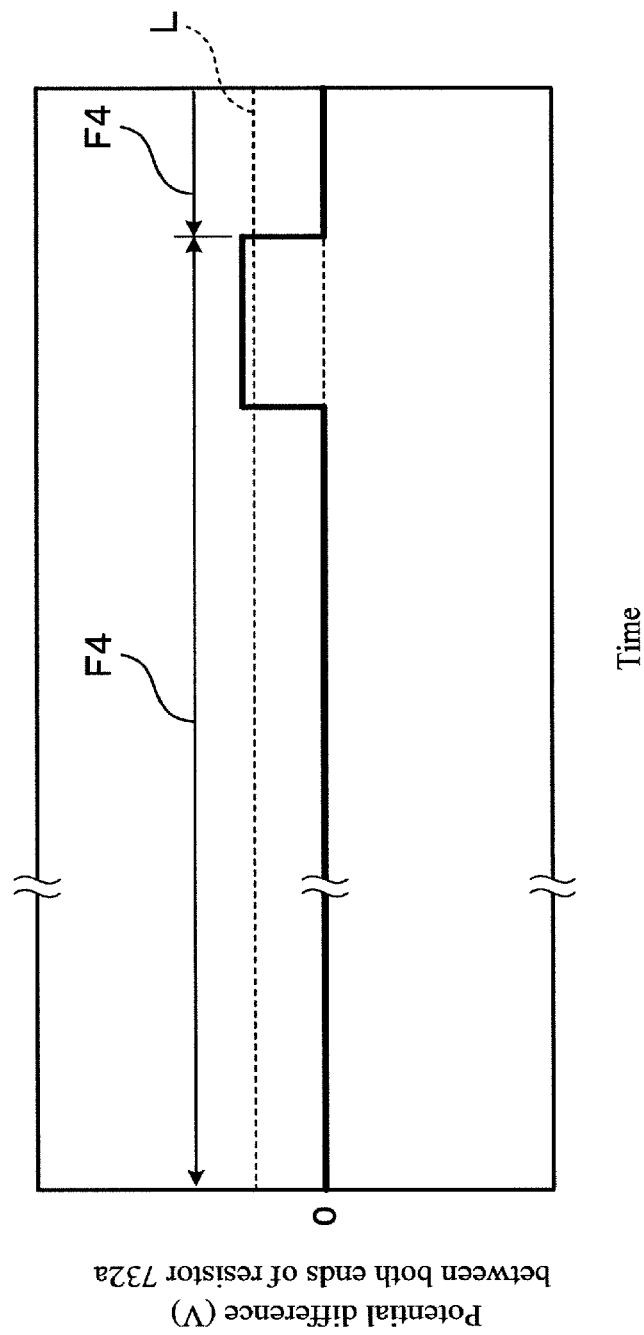
FIG. 11 is a waveform chart showing potential difference produced between both ends of the resistor section in step S5, when the working electrode and the counter electrode of the beauty care instrument described in Example 2 are in contact with a human body.
Figure 12:
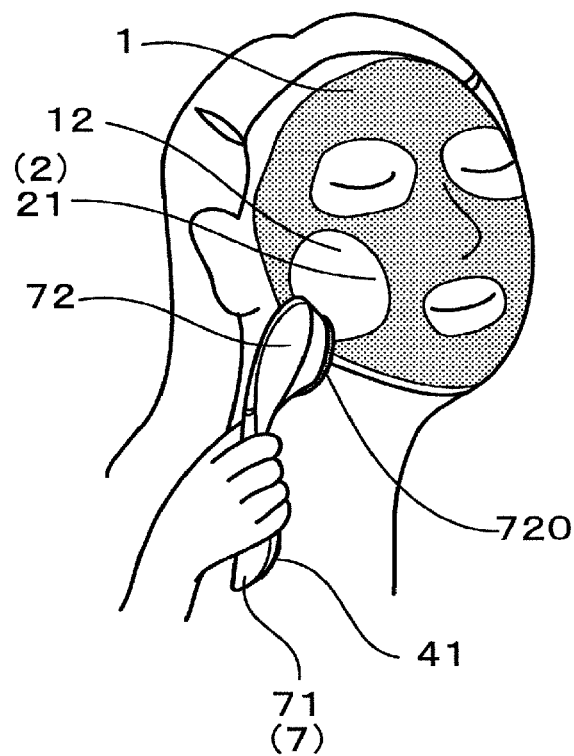
FIG. 12 is a view showing how to remove an aqueous pack agent by use of the beauty care instrument described in Example 2.
Figure 13:
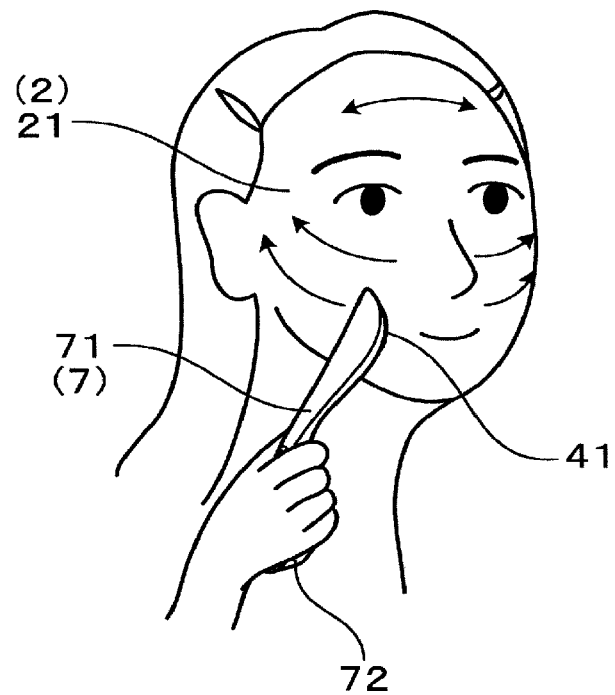
FIG. 13 is a view showing how to apply an iontophoretic current to the skin by use of the beauty care instrument described in Example 2.

Referring to FIG. 4 to FIG. 13, an example of the beauty care instrument to be used in the beauty care method will be described. As shown in FIG. 4, the beauty care instrument 7 has a virtually rod-like body portion 71, an attraction head 72 provided at one of the ends of the body portion 71 and a working electrode 41 provided at the other end of the body portion 71. The attraction head 72 has a magnetic force generation surface 720 for attracting and removing the aqueous pack agent 1 applied to the skin 2 by the magnetic force, as shown in FIG. 6 and FIG. 7. As shown in FIG. 13, the beauty care instrument 7 is constituted in such a design that an iontophoretic current can be supplied to the contact portion at which the working electrode 41 remains in contact with the skin 2. As shown in FIG. 7, the body portion 71 houses a power supply section 733 for supplying a power to the working electrode 41 and a control section 73 for controlling the current to be supplied to the contact portion.

Now, the beauty care instrument 7 will be more specifically described below. As shown in FIG. 4 to FIG. 6, the body portion 71 in the beauty care instrument 7 has the attraction head 72 and a counter electrode 42, which is constituted in such a design that a circular current pathway can be formed between the power supply section 733 and a human body, together with the working electrode 41, at one end. At the other end, the body portion 71 has the working electrode 41. Note that, hereinafter, in the longitudinal direction of the body portion 71, a side on which the working electrode 41 is provided is sometimes referred to as a front side, and a side on which the attraction head 72 is provided is sometimes referred to as a back side. In addition, when the beauty care instrument 7 is viewed along the front-back direction, a side on which the magnetic force generation surface 720 is present is sometimes referred to as a lower side, and a side opposite to the lower side is sometimes referred to as an upper side. Further, a direction perpendicular to both the front-back direction and the upper-lower direction is sometimes referred to as a lateral direction. These directional expressions are designated for convenience sake and nothing to do with actual directions of the beauty care instrument 7 when used.

As shown in FIG. 4 and FIG. 7, the body portion 71 shows a virtually arcuate shape as viewed form the lateral side; more specifically, has a curved shape, in which almost the middle portion in the front-back direction (longitudinal direction) protrudes upwards compared to the both ends. The both ends in the front-back direction of the body portion 71 each have a virtually arc-like outer shape as viewed in the upper-lower direction, as shown in FIG. 5 and FIG. 6. The body portion 71 is formed such that the middle portion in the longitudinal direction is narrower than the both ends, as viewed in the upper-lower direction.

As shown in FIG. 4, the attraction head 72 provided at the back end of the body portion 71 has a bulged portion 721 bulging downward from the body portion 71. The bulged portion 721 has the magnetic force generation surface 720 at a top surface thereof.

As shown in FIG. 7, the bulged portion 721 has the magnetic force generation surface 720 formed of a flat plane and a head sidewall 722 extending from the outer peripheral edge of the magnetic force generation surface 720. As shown in FIG. 6, the magnetic force generation surface 720 has a virtually oval shape as viewed from the lower side and the long axis of the oval is placed along the front-back direction (longitudinal direction). As shown in FIG. 7, the head sidewall 722 is formed in such a way that the wall gradually spreads out upwards from the outer peripheral edge of the magnetic force generation surface 720. The magnetic force generation surface 720 and the head sidewall 722 are connected via a gently curved surface.

As shown in FIG. 7, the bulged portion 721 of the attraction head 72 houses a virtually cylindrical permanent magnet 723. The permanent magnet 723 is disposed in the bulged portion 721 such that one of the magnetic pole faces comes into contact with the inner wall surface of the magnetic force generation surface 720. The other magnetic pole face of the permanent magnet 723 is covered with a yoke material 724 made of a soft magnetic material. In this manner, the beauty care instrument 7 is constituted to more strongly apply the magnetic force generated from the permanent magnet 723 downward.

Note that, the permanent magnet 723 of this example is a neodymium magnet magnetized in the axial direction. Since the neodymium magnet is used, the magnetic flux density, which was measured at a point below the magnetic force generation surface 720 having a distance of 20 mm from the center portion of the surface 720, was 43 mT.

As shown in FIG. 7, the body portion 71 has the counter electrode 42 at the opposite side (upper side) to the magnetic force generation surface 720. As shown in FIG. 6, the working electrode 41 is disposed such that the electrode surface faces to a side on which the magnetic force generation surface 720 is provided (lower side). The working electrode 41 and the counter electrode 42 are each formed such that the width in the lateral direction is narrower than the maximum width of the body portion 71.

As shown in FIG. 7, the body portion 71 houses a power supply section 733, a control section 73, an LED indicator 713 and a vibration motor 714. The power supply section 733 is disposed between the center in the longitudinal direction and the working electrode 41 in the body portion 71, and constituted so as to house a battery 733a in a space within the body portion 71. As shown in FIG. 6 and FIG. 7, the battery 733a is stored within the body portion 71 with the help of a detachable lid portion 733b provided to the body portion 71.

The control section 73 is arranged close to the attraction head 72 from the center of the body portion 71 in the longitudinal direction. As shown in FIG. 5 and FIG. 7, the LED indicator 713, is arranged at a virtually center of the body portion 71 in the longitudinal direction. The LED indicator 713 is constituted to emit light upward when an iontophoretic current flows from the working electrode 41 to the skin 2. The vibration motor 714 is provided within the body portion 71 at the end close to the working electrode 41. The vibration motor 714 is constituted to be driven when an iontophoretic current flows from the working electrode 41 to the skin 2 and generate vibration.

Now, referring to FIG. 8, electrical connection between individual sections in the beauty care instrument 7 will be described. The power supply section 733 is connected to each of a control microcomputer 730 and a voltage applying section 731 in the control section 73, the LED indicator 713 and the vibration motor 714 and supplies a power for operation to each of these sections.

The control section 73 has the control microcomputer 730, the voltage applying section 731 and a reflux section 732. The control section 73 is connected to each of the power supply section 733, the working electrode 41, the counter electrode 42, the LED indicator 713 and the vibration motor 714 and constituted such that operations of these sections can be controlled. The control microcomputer 730 has a function of inputting and outputting signals for controlling the operation of each section. The voltage applying section 731 has a function of applying a voltage between the working electrode 41 and the counter electrode 42. The reflux section 732 has a function of taking in the current flowing through a human body from the working electrode 41 or the counter electrode 42 and returning the current to the power supply section 733.

The control microcomputer 730 and the voltage applying section 731 are mutually connected such that a voltage control signal and a current value selection signal described later can be transmitted. The reflux section 732 is disposed between the voltage applying section 731 and a ground section 731c, which is connected to the negative pole of the power supply section 733. The reflux section 732 is connected to an ADC (Analog to Digital Converter) 730a as described later of the control microcomputer 730. In this way, the control section 73 is constituted such that the potential difference in the reflux section 732 can be input into the control microcomputer 730.

The control microcomputer 730 has the ADC 730a, a calculation section 730b, a signal output section 730c and a delay timer 730d. The ADC 730a has a function of digitalizing the potential difference in the reflux section 732. The calculation section 730b has a function of determining whether the working electrode 41 and the counter electrode 42 are in contact with a human body. The signal output section 730c has a function of controlling the current to be supplied from the working electrode 41 to a skin surface 21 which is desired to produce a beauty effect.

The ADC 730a is connected to the reflux section 732 of the control section 73 and constituted to digitalize the potential difference of the potential of the reflux section 732 from the potential of the ground section 731c (hereinafter the potential of the ground section 731c will be referred to as "ground potential"). The potential difference value digitalized by the ADC 730a is sent to the calculation section 730b in the control microcomputer 730.

In the calculation section 730b, the potential difference value input by the ADC 730a is compared to a predetermined threshold. The calculation section 730b is constituted such that if the potential difference value is less than the predetermined threshold, the calculation section 730b determines that at least one of the working electrode 41 and the counter electrode 42 is not in contact with a human body; whereas, if the potential difference value is the predetermined threshold or more, the calculation section 730b determines that the working electrode 41 and the counter electrode 42 are both in contact with a human body. Also, the calculation section 730b is constituted such that the section 730b can control the signal output from the signal output section 730c based on both of the determination results and the preset operation flow shown in FIG. 9 and FIG. 10. Note that, the operation flow is more specifically described later.

The signal output section 730c is constituted to receive a control signal from the calculation section 730b and then output a voltage control signal and a current value selection signal to the voltage applying section 731. The voltage control signal is input into a polarity inverting circuit 731a described later in the voltage applying section 731 and controls on-off and polarity of the voltage to be applied between the working electrode 41 and the counter electrode 42. The current value selection signal is input into a constant current circuit 731b described later in the voltage applying section 731 and controls the value of current flowing between the working electrode 41 and the counter electrode 42.

The signal output section 730c is also connected to the LED indicator 713 and the vibration motor 714. The signal output section 730c is constituted such that if the calculation section 730b determines that the working electrode 41 and the counter electrode 42 are both in contact with a human body, the signal output section 730c outputs individual signals for emitting the LED indicator 713 and driving the vibration motor 714.

The delay timer 730d is driven by the calculation section 730b if the calculation section 730b determines that at least one of the working electrode 41 and the counter electrode 42 is not in contact with a human body. The delay timer 730d has a function of stopping operation of the calculation section 730b for a predetermined time. Owing to the function, in the beauty care instrument 7, operations of individual sections are stopped in accordance with the stop in operation of the calculation section 730b for the predetermined time from the starting up of the delay timer 730d. The delay timer 730d is constituted to restart the calculation section 730b after the passage of the predetermined time.

The voltage applying section 731 has the polarity inverting circuit 731a and the constant current circuit 731b, which are mutually connected. The polarity inverting circuit 731*a* and the signal output section 730*c* of the control microcomputer 730 are mutually connected. The polarity inverting circuit 731*a* is connected to each of the working electrode 41 and the counter electrode 42. Accordingly, the polarity inverting circuit 731*a* is constituted such that the potential difference between the working electrode 41 and the counter electrode 42 can be controlled based on the voltage control signal output from the signal output section 730*c*.

The constant current circuit 731*b* has a function of maintaining the current flowing between the working electrode 41 and the counter electrode 42 to be constant. The constant current circuit 731*b* and the signal output section 730*c* of the control microcomputer 730 are mutually connected. The constant current circuit 731*b* is constituted such that the current flowing between the working electrode 41 and the counter electrode 42 can be set at two levels, based on the current value selection signal output from the signal output section 730*c*. In this example, the current value of the current is set at two levels: iontophoresis level and skin care level, which is lower than the iontophoresis level. Note that, the iontophoresis level is applied during the operations in iontophoresis step S8 and reset pulse step S9; whereas, the skin care level is applied during the operation of skin care step S11.

The reflux section 732 has a resistor 732*a* connected between the voltage applying section 731 and the ground section 731*c*. Owing to this, the current taken from the voltage applying section 731 flows through the resistor 732*a* toward the ground section 731*c* and passes through the ground section 731*c* to the negative pole of the power supply section 733. A point between the voltage applying section 731 and resistor 732*a* in the reflux section 732 is connected to the ADC 730*a* of the control microcomputer 730. Owing to this, the ADC 730*a* is constituted such that the potential difference between the potential of a point between the voltage applying section 731 and the resistor 732*a* and the ground potential is input.

Now, referring to FIG. 9 and FIG. 10, the operational flow of the beauty care instrument 7 will be described. When a power is supplied to the beauty care instrument 7 from the power supply section 733, an initialization of the control microcomputer 730 is carried out (step S1). At this time, the control microcomputer 730 outputs a current value selection signal to the constant current circuit 731*b* to set the current value at the iontophoresis level.

Thereafter, the control microcomputer 730 turns on the delay timer 730*d* and executes step S2 of waiting the elapse of the predetermined time. Note that the predetermined time can be appropriately set within the range of 50 to 1000 milliseconds by the delay timer 730*d* of this example.

Following step S2, the control microcomputer 730 executes step S3 for supplying the power for operation from the power supply section 733 to the voltage applying section 731; at the same time, a voltage control signal is output from the signal output section 730*c*. Owing to the operation, while the control microcomputer 730 controls the potential difference between two electrodes such that the potential of the working electrode 41 is lower than that of the counter electrode 42 and applies a pulse voltage once between the two electrodes. In this manner, step S4 of applying a pulse voltage once between the working electrode 41 and the counter electrode 42 is carried out. In this example, the value of the pulse voltage in step S4 was specified to be 5V.

Figure 9:
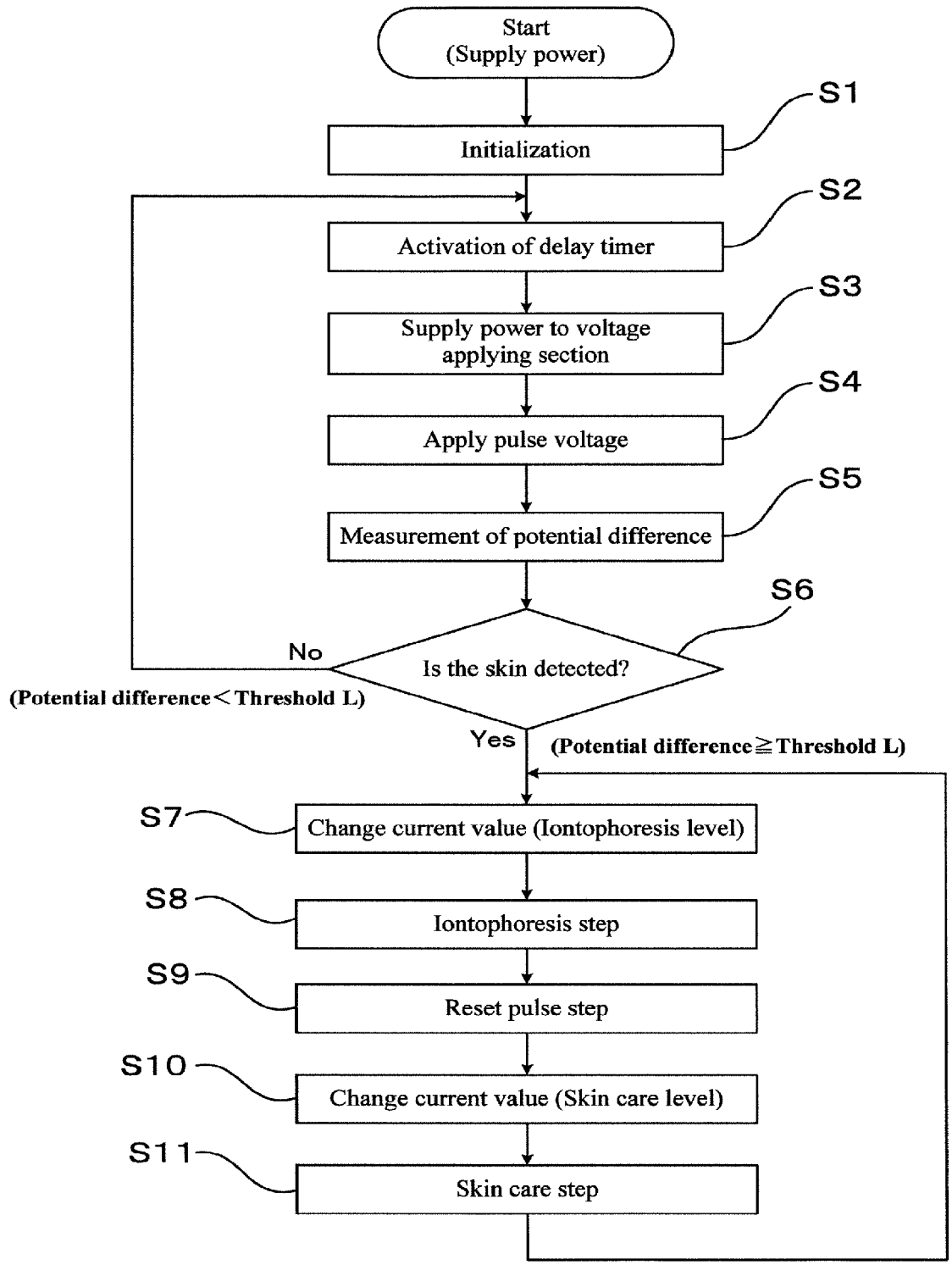
FIG. 9 is a flowchart showing the operation of the beauty care instrument described in Example 2.

Subsequently, as shown in FIG. 9, step S5 of measuring the potential difference in the reflux section 732 is carried out. In step S5, when the working electrode 41 and the counter electrode 42 are both in contact with the skin 2, a pulse current ascribed to the pulse voltage flows from the counter electrode 42 to the working electrode 41 via a human body. The pulse current is taken from the working electrode 41 into the control section 73 and produces the potential difference between both ends of resistor 732*a* in the reflux section 732, like waveform F4 shown in FIG. 11. The potential difference produced between the both ends of the resistor 732*a*, in other words, the potential difference of the reflux section 732 from the ground potential is input into the ADC 730*a* of the control microcomputer 730 and the value is measured.

In contrast, when at least one of the working electrode 41 and the counter electrode 42 is not in contact with the skin 2, even if the pulse voltage is applied, no current flows through the resistor 732*a*, with the result that no potential difference is produced between the both ends of the resistor 732*a*. Because of this, when at least one of the working electrode 41 and the counter electrode 42 is not in contact with the skin 2, the value of the potential difference becomes 0 V.

Thereafter, the control microcomputer 730 executes step S6 of determining whether the working electrode 41 and the counter electrode 42 are in contact with a human body based on the results of comparison between the potential difference and a predetermined threshold L (see, FIG. 11) in the calculation section 730*b*. If the potential difference obtained in step S5 is less than threshold L, the control microcomputer 730 determines that at least one of the working electrode 41 and the counter electrode 42 is not in contact with a human body ("No" in Step S6). In this case, the control microcomputer 730 instructs to go back to step S2 of driving the delay timer 730*d*. The control microcomputer 730 executes step S2 to step S6 repeatedly as long as it is determined that at least one of the working electrode 41 and the counter electrode 42 is not in contact with a human body in step S6. Note that, in this example, threshold L can be appropriately set between 50 to 200 mV.

In contrast, as shown in FIG. 11, if the potential difference of the reflux section 732 from the ground potential is threshold L or more in step S6, the control microcomputer 730 determines that the working electrode 41 and the counter electrode 42 are both in contact with a human body ("Yes" in step S6). In this case, as shown in FIG. 9, the control microcomputer 730 executes step S7 of inputting a current value selection signal into the constant current circuit 731*b* to set the current value at the iontophoresis level. Following step S7, the control microcomputer 730 sends a voltage control signal, which instructs to supply an iontophoretic current from the working electrode 41 to the skin 2, to the voltage applying section 731.

As shown in FIG. 9, the iontophoretic current is constituted to sequential repeats of iontophoresis step S8 of supplying a single-polarity current to a portion at which the working electrode 41 is in contact with the skin 2 (F1, FIG. 2); reset pulse step S9 of supplying a pulse current of the other polarity to the contact portion (F2, FIG. 2); and skin care step S11 of supplying a current in which polarity alternately changes to the contact portion (F3, FIG. 2). In this procedure, the waveform of the iontophoretic current flowing through the skin 2 is constituted of repeats of basic waveforms F1 to F3 as shown in FIG. 2.

Figure 10:
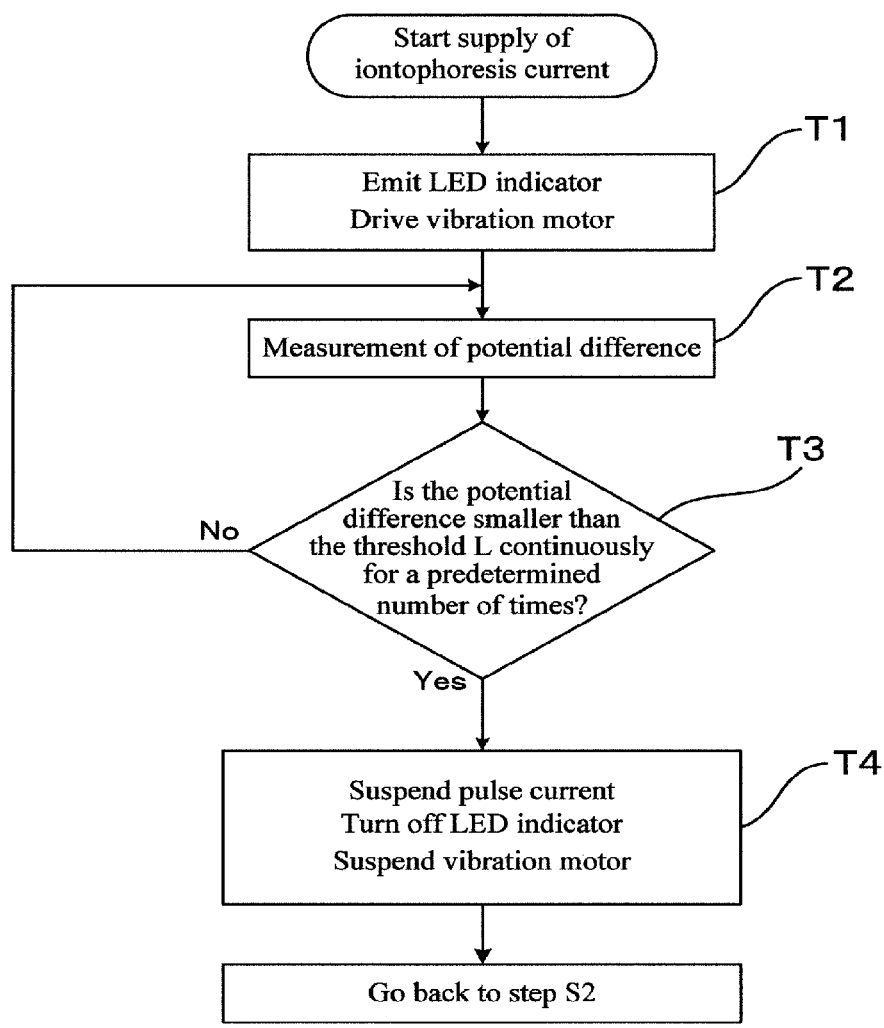
FIG. 10 is a flowchart showing the operation of a skin detecting function while iontophoretic current flows, described in Example 2.

The control microcomputer 730 outputs a drive signal from the signal output section 730*c* to the LED indicator 713 and the vibration motor 714 as long as the iontophoretic current flows through the skin 2 (step T1, FIG. 10). Owing to this, the LED indicator 713 and the vibration motor 714 are driven as long as the working electrode 41 and the counter electrode 42 are both in contact with a human body.

To describe more specifically, in iontophoresis step S8, the control microcomputer 730 controls the potential difference between two electrodes such that the potential of the working electrode 41 is lower than the potential of the counter electrode 42; at the same time, a pulse voltage is applied between the two electrodes in plurality of times. Owing to this, the working electrode 41 can supply a negative-polarity pulse current like the basic waveform F1 shown in FIG. 2 to the skin 2, a plurality of times.

In reset pulse step S9, the control microcomputer 730 controls the potential difference between two electrodes such that the potential of the working electrode 41 is higher than the potential of the counter electrode 42; at the same time, a pulse voltage is once applied between the two electrodes. Owing to this, the working electrode 41 can supply a positive-polarity pulse current like the basic waveform F2 shown in FIG. 2 to the skin 2.

Following reset pulse step S9, the control microcomputer 730 executes step S10 of outputting a current value selection signal to the constant current circuit 731b to set a current value at the skin care level, as shown in FIG. 9.

Following step S10, the control microcomputer 730 executes skin care step S11, as shown in FIG. 9. In skin care step S11, the control microcomputer 730 applies a square wave, in which the high and low of potential difference of the working electrode 41 to the counter electrode 42 alternately changes, to the two electrodes. Owing to this, the working electrode 41 can supply a square wave current, in which a positive polarity and a negative polarity alternately change like basic waveform F3 shown in FIG. 2 to the skin 2.

As shown in FIG. 10, the control microcomputer 730 has a skin detecting function, which carries out determination as to whether the working electrode 41 and the counter electrode 42 are in contact with a human body by use of the pulse of an iontophoretic current flowing through the skin 2, in parallel to step S7 to S11. In other words, the control microcomputer 730 is constituted such that step T2 of measuring the potential difference of the reflux section 732 (produced due to the pulse current) from the ground potential is carried out by using the pulse current flowing through the skin 2 in iontophoresis step S8, reset pulse step S9 and skin care step S11, similarly to step S5.

As shown in FIG. 10, the control microcomputer 730 executes step T3 of determining the contact state whether the working electrode 41 and the counter electrode 42 are in contact with a human body based on the results of measuring the potential difference of the reflux section 732. The determination in step T3 as to the contact state whether the working electrode 41 and the counter electrode 42 are in contact with a human body may be made based on the measurement result of potential difference from a single pulse current, or total of measurement results of potential differences from a plurality of pulse currents. Furthermore, the pulse current to be used in determination of the contact state can be appropriately selected from the pulse currents in iontophoresis step S8, reset pulse step S9 and skin care step S11.

In this example, for example, the determination of the contact state in step T3 is made based on the determination whether or not the potential difference values between both ends of the resistor 732a due to a pulse current (F2, FIG. 2) in reset pulse step S9 are continuously lower than threshold L, at predetermined number of times. In other words, if the potential difference values due to a pulse current (F2, FIG. 2) are continuously less than threshold L ("Yes", step T3,) at predetermined number of times, the control microcomputer 730 of this example determines that at least one of the working electrode 41 and the counter electrode 42 is not in contact with a human body. In this case, the control microcomputer 730 terminates supply of the iontophoretic current and simultaneously terminates output of a drive signal to the LED indicator 713 and the vibration motor 714 (step T4). The control microcomputer 730 is constituted to repeat step S2 to step S6 (shown in FIG. 9) after step T4.

In contrast, as long as the number of cases where the potential difference values are continuously less than threshold L, does not reach predetermined number of times ("No", step T3), the control microcomputer 730 determines that the working electrode 41 and the counter electrode 42 are both in contact with a human body. As long as the control microcomputer 730 determines that the working electrode 41 and the counter electrode 42 are both in contact with a human body in step T3, the control microcomputer 730 repeatedly executes step S7 to step S11 shown in FIG. 9.

Next, how to use the beauty care instrument 7 will be described.

After the user applies the aqueous pack agent 1, the user holds the body portion 71 at the side of the working electrode 41 and makes the magnetic force generation surface 720 of the attraction head 72 closer to the skin 2, as shown in FIG. 12. In this case, a detachable cover member may be provided to the magnetic force generation surface 720 in advance. The shape, material and others of the cover member are not particularly limited as long as the member can cover the magnetic force generation surface 720 and any type of cover member may be used. In this example, the attraction head 72 is wrapped with cotton sheet (not shown in the figure).

By this operation, dirt 200 of the skin 2 and others is removed together with the magnetic powder 11 from the skin surface 21 and attracted by the attraction head 72, as mentioned above. After the aqueous pack agent 1 removed from the skin surface 21, the aqueous solution 12 containing the iontophoretic component 13 remains applied on the skin 2. Note that, the used aqueous pack agent 1 attracted by the attraction head 72 can be removed together with the cover member from the magnetic force generation surface 720 and discarded.

After the used aqueous pack agent 100 and others are removed from the skin 2, as mentioned above, the user shifts the position of the body portion 71 to be held such that the working electrode 41 protrudes from the hand and the counter electrode 42 comes into contact with the hand. Then, the working electrode 41 is allowed to touch the skin surface 21, as shown in FIG. 13. Owing to the operation, through the contact portion of the working electrode 41 in contact with the skin 2, the iontophoretic current, which consists of repeats of basic waveform F1 to F3 shown in FIG. 2, flows. Note that, in this example, in iontophoresis step S8, the working electrode 41 serves as a cathode; whereas, the counter electrode 42 serves as an anode, and a negative-polarity current flows to the skin surface 21 in contact with the working electrode 41. In this manner, the beauty care instrument 7 allows L-ascorbic acid 2-phosphate ion 131 (anion) to infiltrate into the skin.

Now, the effect of the beauty care instrument 7 will be described. The beauty care instrument 7 has the attraction head 72 for attracting and removing the aqueous pack agent 1 by the magnetic force. Owing to this, as shown in FIG. 12, when the user holds the body portion 71 and approaches the attraction head 72 to the skin surface 21 to which the aqueous pack agent 1 is applied, the aqueous pack agent 1 is attracted by the attraction head 72 with the help of the magnetic force. As a result, the beauty care instrument 7 can easily remove the used aqueous pack agent 1.

As shown in FIG. 4, the beauty care instrument 7 has the working electrode 41 for supplying an iontophoretic current to the contact portion while the electrode 41 remains in contact with the skin 2. Accordingly, when the user brings the working electrode 41 into contact with the skin 2 to which a charged beauty component is previously applied, and then an iontophoretic current is supplied, as mentioned above, the beauty component easily migrates into the skin. As a result, the beauty care instrument 7 facilitates infiltration of the beauty component and easily and immediately exerts a beauty effect.

The beauty care instrument 7 has both the attraction head 72 and the working electrode 41. Accordingly, as mentioned above, a working step of removing dirt of the skin 2 and waste with the aqueous pack agent 1 and a working step of allowing a charged beauty component to infiltrate into the skin by an iontophoretic current can be carried out by using one instrument. As a result, it is not necessary for the user to individually prepare instruments for the two working steps and select the instrument depending upon the use.

As shown in FIG. 4, the attraction head 72 has the magnetic force generation surface 720 facing in the direction in virtually perpendicular to the longitudinal direction of the body portion 71 (down side). Accordingly, it is easy for the user to face the magnetic force generation surface 720 towards the skin 2 to which the aqueous pack agent 1 is applied just by holding the body portion 71, as shown in FIG. 12. As a result, the user can extremely conveniently use the beauty care instrument 7.

As shown in FIG. 7, the body portion 71 has the counter electrode 42 on the opposite (upper) side of the magnetic force generation surface 720, and the working electrode 41, which is arranged so as to face down, as shown in FIG. 6. Accordingly, when the user puts the beauty care instrument 7 on a table or the like, the possibility of electrical conduction between the working electrode 41 and the counter electrode 42 via the surface of the table can be reduced, as mentioned above, with the result that the power consumption of the beauty care instrument 7 tends to be reduced. In addition, since a circular current pathway is formed between the power supply section 733 and a human body, the beauty care instrument 7 can more efficiently supply an iontophoretic current to the human body. As a result, the beauty care instrument 7 can further improve a beauty effect.

Figure 8:
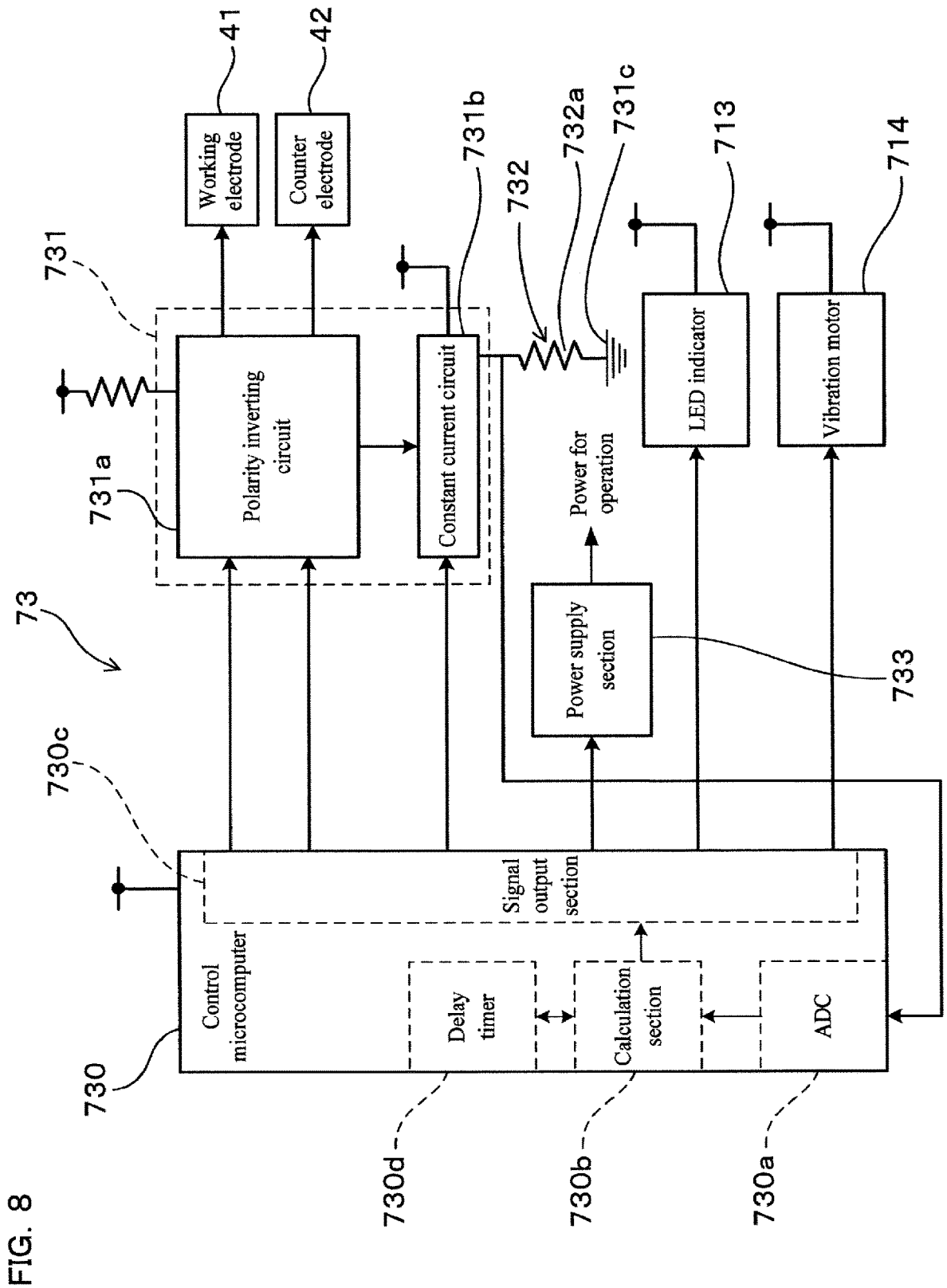
FIG. 8 is a block diagram describing the constitution of the control section of the beauty care instrument described in Example 2.

As shown in FIG. 8 and FIG. 9, the control section 73 has a means for applying a pulse voltage to the working electrode 41 to measure an electrical characteristic value within the control section 73 based on the pulse voltage, a means for determining whether the working electrode 41 and the counter electrode 42 are in contact with a human body based on the electrical characteristic value, and a means for supplying an iontophoretic current to the contact portion if the working electrode 41 and the counter electrode 42 are determined to be both in contact with a human body; and constituted such that if it is determined that at least one of the working electrode 41 and the counter electrode 42 is not in contact with a human body, after the passage of a predetermined time measured by the delay timer 730*d*, measurement of the electrical characteristic value and determination are repeated again.

Accordingly, the beauty care instrument 7 can supply an iontophoretic current to the contact portion at the time when the working electrode 41 and the counter electrode 42 are both in contact with a human body, without turning on/off a switch. Owing to this, the user can obtain the effect of facilitating infiltration of a beauty component simply by holding the body portion 71 at the side of the counter electrode 42 and touching the counter electrode 42 with a hand; and simultaneously bringing the working electrode 41 into contact with a portion at which a beauty effect is desired.

The beauty care instrument 7 can reduce a frequency of measurement of the electrical characteristic value and the determination as mentioned above by operating the delay timer 730*d* in the aforementioned manner. As a result, in the beauty care instrument 7, power consumption in the standby state, in other words, in the state where at least one of the working electrode 41 and the counter electrode 42 is not in contact with a human body, can be reduced.

As shown in FIG. 8 and FIG. 9, the control section 73 has the reflux section 732, which takes in the current flowing through a human body and sends the current to the power supply section 733; and is constituted such that the potential difference of the reflux section 732 from the ground potential is measured as an electrical characteristic value and if the potential difference is a predetermined threshold or more, it is determined that the working electrode 41 and the counter electrode 42 are both in contact with a human body. Accordingly, the circuit design of the control section 73 can be easily simplified, as mentioned above; at the same time, the accuracy in determining that the working electrode 41 and the counter electrode 42 are in contact with a human body can be improved.

As shown in FIG. 2 and FIG. 9, the iontophoretic current is constituted of sequential repeats of iontophoresis step S8 of supplying a single-polarity current (FIG. 2, F1) to the contact portion; reset pulse step S9 of supplying a pulse current (FIG. 2, F2) having the other polarity to the contact portion; and skin care step S11 of supplying current (FIG. 2, F3), in which polarity alternately changes, to the contact portion. Accordingly, as mentioned above, it is expected that the beauty effect can be further improved by the beauty care instrument 7 since an effect of facilitating infiltration of a beauty component into the skin and an effect of activating the skin 2 are synergetically exerted.

The beauty care instrument 7 has the vibration motor 714 at the edge close to the working electrode 41 and constituted such that the vibration motor 714 is driven while an iontophoretic current flows through the skin 2. Thus, owing to vibration generated from the vibration motor 714, effects such as a lymph-flow improvement effect, a blood-circulation improvement effect and a metabolism improving effect, may be obtained in the portion at which the working electrode 41 is in contact with the skin 2 and the portion around them. As a result, the beauty care instrument 7 can contribute to further improvement of the beauty effect that the user feels.

As described in the foregoing, the beauty care instrument 7 successfully improves convenience in continuously carrying out a work step of removing dirt of skin and waste and a work step of allowing a beauty component to infiltrate into the skin.

Figure 14:
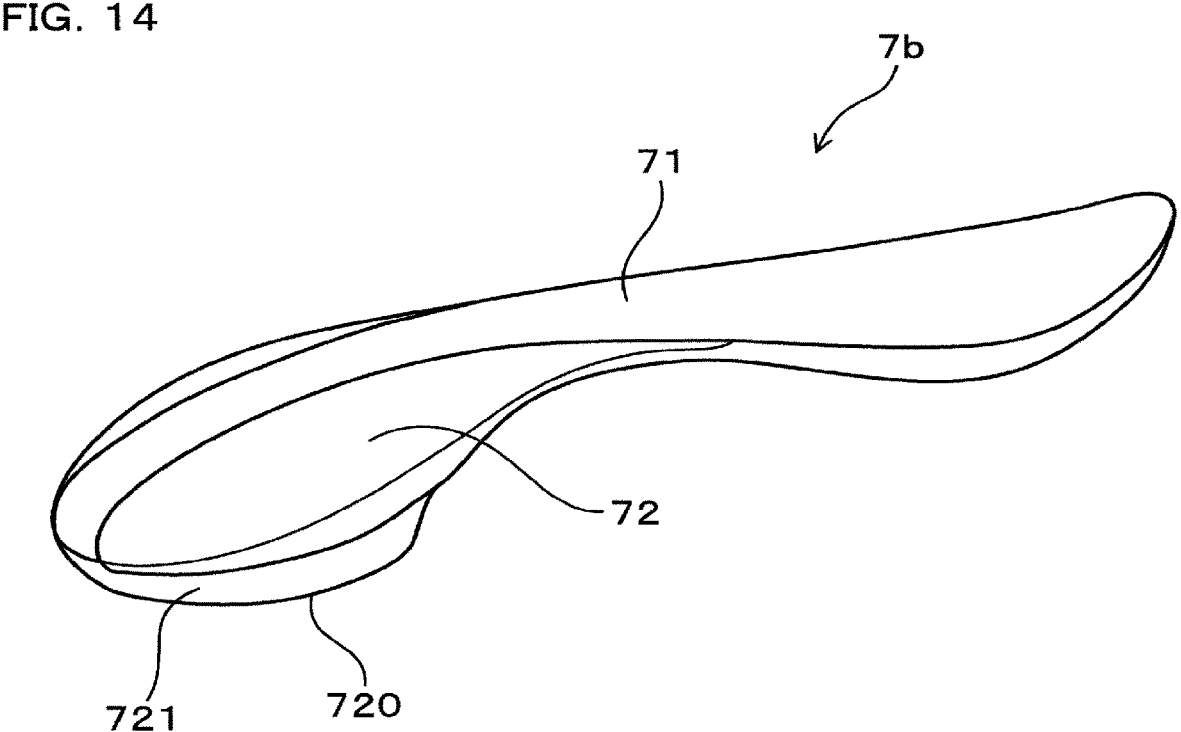
FIG. 14 is a perspective view of the beauty care instrument in attracting and removing a magnetic powder, as viewed obliquely from upward.
Figure 15:
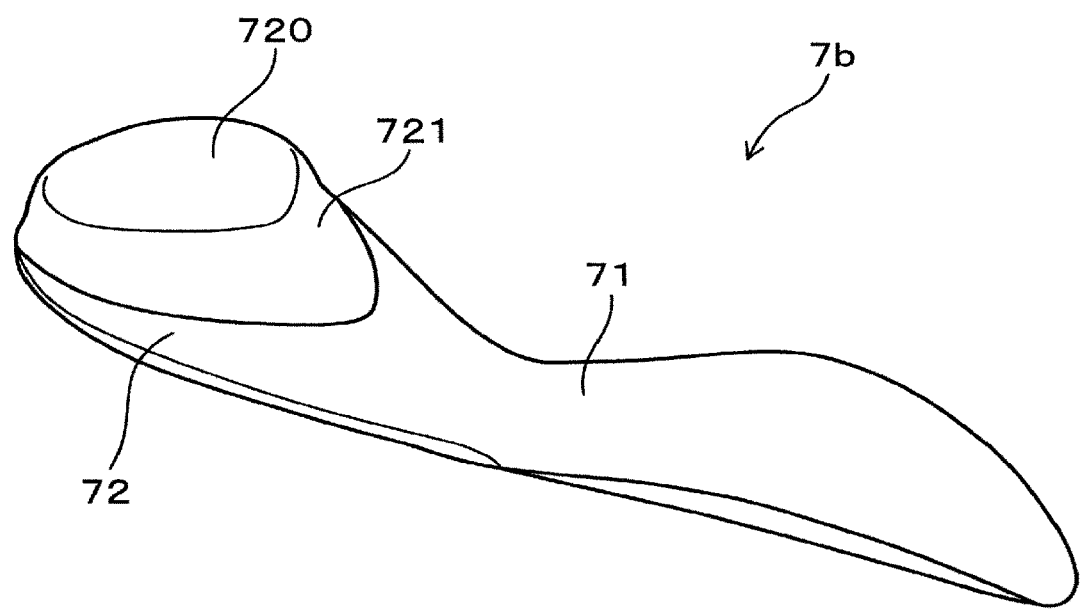
FIG. 15 is a perspective view of the beauty care instrument in attracting and removing a magnetic powder, as viewed obliquely from downward.

Note that, Example 2 shows an example of the beauty care instrument 7 having the attraction head 72 for attracting and removing the magnetic powder 11 by the magnetic force and also constituted as an iontophoretic instrument for supplying an iontophoretic current to the skin 2. However, a work step of attracting the magnetic powder 11 and an iontophoretic step can be carried out by using different instruments. For example, as shown in FIG. 14 and FIG. 15, a work step of attracting the magnetic powder 11 can be carried out by the beauty care instrument 7b having the attraction head 72 alone without providing e.g. the working electrode 41 or the control section 73. Note that, of the reference numerals used in FIG. 14 and FIG. 15, the same reference numerals used in Example 2 designate the same structural elements corresponding to those used in Example 2.

As is not shown in the figures, for example, iontophoresis can be carried out by the beauty care instrument 7 having e.g., the working electrode 41 and the control section 73 without providing the attraction head 72. The shape of the beauty care instrument 7 is not limited to that shown in Example 2 and can be variously modified. For example, the body portion 71 may have a spherical or cylindrical shape.

The invention claimed is:

1. A beauty care method comprising:
    applying an aqueous pack agent comprising water, a magnetic powder, a thickener and a charged iontophoretic component to the skin;
    applying magnetic force to the magnetic powder in the aqueous pack agent applied to the skin to attract and remove the magnetic powder from the skin surface while leaving an aqueous solution of the iontophoretic component on the skin surface; and
    applying an iontophoretic current to the skin with the aqueous solution left to allow the iontophoretic component to infiltrate into the skin.

2. The beauty care method according to claim 1, wherein the aqueous pack agent comprises 5 to 73 mass % of water and 15 to 80 mass % of the magnetic powder.

3. The beauty care method according to claim 1, wherein the aqueous pack agent comprises 10 to 45 mass % of glycerin as the thickener.

4. The beauty care method according to claim 1, wherein the aqueous pack agent has an electrical conductivity of 20 µS/cm or more at 25° C.

5. The beauty care method according to claim 1, wherein the aqueous pack agent has a viscosity of 9,000 mPa·s or more.

6. The beauty care method according to claim 1, the magnetic powder having:
    a mean volume particle diameter being 50 to 75 µm as determined from a particle size distribution obtained by a laser diffraction scattering method;
    a content of particles with a particle diameter being less than 37 µm of 15 mass % or less; and
    a content of particles with a particle diameter being 105 µm or more of 5 mass % or less.

7. The beauty care method according to claim 1, wherein the magnetic powder has a saturation magnetization of 80 $Am^2/kg$ or more.

8. The beauty care method according to claim 1, wherein the magnetic powder is constituted of a ferromagnetic metal and an oxidation resistant film is formed on surfaces of particles constituting the magnetic powder.

9. The beauty care method according to claim 1, wherein the magnetic powder contains a ferromagnetic ferrite as a main component.

10. The beauty care method according to claim 9, wherein the magnetic powder contains a chemical component comprising 80 mass % or more of a magnetite and a balance being wustite, hematite and inevitable impurities.

11. A beauty care method comprising:
    applying an aqueous pack agent to the skin wherein said aqueous pack agent comprises a water-soluble solvent, a magnetic powder, a thickener and a component to be ionized to generate an iontophoretic component;
    applying magnetic force to the magnetic powder in the aqueous pack agent applied to the skin to attract and remove the magnetic powder from the skin surface while leaving the iontophoretic component on the skin surface; and
    applying an iontophoretic current to the skin to allow the iontophoretic component to infiltrate into the skin.

* * * * *